(12) United States Patent
Kumar et al.

(10) Patent No.: US 11,807,673 B2
(45) Date of Patent: *Nov. 7, 2023

(54) METHODS AND COMPOSITIONS FOR INCREASING RED BLOOD CELLS

(71) Applicant: Acceleron Pharma Inc., Cambridge, MA (US)

(72) Inventors: Ravindra Kumar, Acton, MA (US); Rajasekhar Naga Venkata Sai Suragani, Norwood, MA (US); John Knopf, Carlisle, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/063,848

(22) Filed: Oct. 6, 2020

(65) Prior Publication Data

US 2021/0277082 A1    Sep. 9, 2021

Related U.S. Application Data

(63) Continuation of application No. 16/422,117, filed on May 24, 2019, now Pat. No. 10,829,534, which is a continuation of application No. 15/783,056, filed on Oct. 13, 2017, now Pat. No. 10,344,066, which is a continuation of application No. 13/827,477, filed on Mar. 14, 2013, now Pat. No. 9,809,636.

(60) Provisional application No. 61/621,154, filed on Apr. 6, 2012.

(51) Int. Cl.
  *C07K 14/51*    (2006.01)
(52) U.S. Cl.
  CPC .......... *C07K 14/51* (2013.01); *C07K 2319/02* (2013.01)
(58) Field of Classification Search
  CPC .......................... C07K 14/51; C07K 2319/02
  See application file for complete search history.

(56) References Cited

U.S. PATENT DOCUMENTS

| | | | |
|---|---|---|---|
| 5,703,043 A | 12/1997 | Celeste et al. | |
| 6,034,062 A | 3/2000 | Thies et al. | |
| 6,287,816 B1 | 9/2001 | Rosen et al. | |
| 7,960,343 B2 | 6/2011 | Knopf et al. | |
| 8,367,611 B2 | 2/2013 | Knopf et al. | |
| 8,743,601 B2 | 6/2014 | Suguro | |
| 9,353,356 B2 | 5/2016 | Knopf et al. | |
| 9,526,759 B2 | 12/2016 | Knopf et al. | |
| 9,809,636 B2 | 11/2017 | Kumar et al. | |
| 10,344,066 B2 | 7/2019 | Kumar et al. | |
| 2003/0224501 A1 | 12/2003 | Young et al. | |
| 2014/0056902 A1 | 2/2014 | Shimizu et al. | |

FOREIGN PATENT DOCUMENTS

| | | |
|---|---|---|
| WO | WO-93/00432 A1 | 1/1993 |
| WO | WO-94/20539 A1 | 9/1994 |
| WO | WO-94/26893 A1 | 11/1994 |
| WO | WO-2005/113590 A2 | 12/2005 |
| WO | WO-2006/105359 A2 | 10/2006 |
| WO | WO-2008/015383 A2 | 2/2008 |
| WO | WO-2008/076437 A2 | 6/2008 |
| WO | WO-2009/114180 A1 | 9/2009 |
| WO | WO-2009/158015 A2 | 12/2009 |
| WO | WO-2009/158033 A2 | 12/2009 |
| WO | WO-2011/020045 A1 | 2/2011 |
| WO | WO-2016/183280 A1 | 11/2016 |

OTHER PUBLICATIONS

Brown et al., "Crystal structure of BMP-9 and functional interactions with pro-region and receptors," The Journal of Biological Chemistry, vol. 280(26): 25111-25118 (2005).

International Search Report PCT/US2013/035305 dated Jun. 4, 2013.

Tokuriki, N., et al., "Stability effects of mutations and protein evolvability," Current Opinion in Structural Biology, 19:596-604 (2009).

Truksa et al., "Bone morphogenetic proteins 2, 4, and 9 stimulate murine hepcidin 1 expression independently of Hfe, transferrin receptor 2 (Tfr2), and IL-6," PNAS, vol. 103(27): 10289-10293 (2006).

*Primary Examiner* — Robert S Cabral

(74) *Attorney, Agent, or Firm* — Su Kyung Suh; Anna L. Cocuzzo

(57) ABSTRACT

In certain aspects, the present invention provides compositions and methods for increasing red blood cell and/or hemoglobin levels in vertebrates, including rodents and primates, and particularly in humans.

19 Claims, 3 Drawing Sheets

Specification includes a Sequence Listing.

BMP9 Multiple Sequence Alignment

```
human    MCPGALWVALPLLSLLAGSLQGKPLQSWGRGSAGGNAHSPLGVPGGGLPEHTFNLKMFLE 60
murine   MSPGAFRVALLPLFLLVCVTQQKPLQNWEQASPGENAHSSLGLSGAGE-EGVFDLQMFLE 59
chicken  MHYFGVLAALSVFNIIACLTRGKPLENWKKLPVMEESDAFFHDPGEVEHDTHFDFKSFLE 60
         *   .. .  : ::.     : *:.* :  .   ::.: :  .*    : *::: *** human    NVKVDFLRSLNLSGVPSQDKTRVEPPQYMIDLYNRYTSDKSTTPASNIVRSFSMEDAISI 120
murine   NMKVDFLRSLNLSGIPSQDKTPAEPPQYMIDLYNRYTTDKSSTPASNIVRSFSVEDAIST 119
chicken  NMKTDLLRSLNLSRVPSQVKTKEEPPQFMIDLYNRYTADKSSIPASNIVRSFSTEDVVSL 120
         *:*.*:***** :* : :****:*:******** .:* human    TATEDFPFQKHILLFNISIPRHEQITRAELRLYVSCQNHVDPSHDLKGSVVIYDVLDGTD 180
murine   AATEDFPFQKHILIFNISIPRHEQITRAELRLYVSCQNDVDSTHGLEGSMVVYDVLEDSE 179
chicken  ISPEEHSFQKHILLFNISIPRYEEVTRAELRIFISCHKEVGSPSRLEGNMVIYDVLDG-D 179
          :.*:..****** :*******:*:******::::**::.*...  *:*.:*:****:. :

human    AWDSATETKTFLVSQDIQDEGWETLEVSSAVKRWVRSDSTKSKNKLEVTVESHRKG---C 237
murine   TWDQATGTKTFLVSQDIRDEGWETLEVSSAVKRWVRADSTTNKNKLEVTVQSHRES----C 236
chicken  HWENKESTKSLLVSHSIQDCGWEMFEVSSAVKRWVKADKMKTKNKLEVVIESKDLSGFPC 239
          *:..   ::*:.*:* *  :********::*.  ..******.::*:    .   * human    DTLDISVPPGSRNLPFFVVFSNDHSSGTKETRLELREMISHEQESVLKKLSKDGSTEAGE 297
murine   DTLDISVPPGSKNLPFFVVFSNDRSNGTKETRLELKEMIGHEQETMLVKTAKNAYQVAGE 296
chicken  GKLDITVTHDTKNLPLLIVFSNDRSNGTKETKVELREMIVHEQESVLNKLGKNDSSEEE 299
         ..***:*. .::*::***:*.***::::*: * .*:           * human    SSHEEDTDGHVAAGSTLARRKRSAGAGSHCQKTSLRVNFEDIGWDSWIIAPKEYEAYECK 357
murine   SQEEEGLDGYTAVGPLLARRKRSTGASSHCQKTSLRVNFEDIGWDSWIIAPKEYDAYECK 356
chicken  QREEKAIARPRQHS----SRSKRSIGAN-HCRRTSLHVNFKEIGWDSWIIAPKDYEAFECK 355
          . .*:       .     :* * . ::*:*::*******::*:*:*** human    GGCFFPLADDVTPTKHAIVQTLVHLKFPTKVGKACCVPTKLSPISVLYKDDMGVPTLKYH 417
murine   GGCFFPLADDVTPTKHAIVQTLVHLKFPTKVGKACCVPTKLSPISILYKDDMGVPTLKYH 416
chicken  GGCFFPLTDNVTPTKHAIVQTLVHLQNPKKASKACCVPTKLDAISILYKDDAGVPTLIYN 415
         *******:*:***********.*.*..*********..**:***** *****  *:

human    YEGMSVAECGCR 429  (SEQ. ID. NO:1)
murine   YEGMSVAECGCR 428  (SEQ. ID. NO:7)
chicken  YEGMKVAECGCR 427  (SEQ. ID. NO:8)
         ****.*******
```

FIGURE 1

BMP10 Multiple Sequence Alignment

```
Human_BMP10    MGSLVLTLCALFCLAAYLVSGSPIMNLEQSPLEEDMSLFGDVFSEQDGVDFNTLLQSMKD
Murine_BMP10   MGSLVLPLSAVFCLVAHSASGSPIMGLEQSPLEEDMPFFDDIFTEQDGIDFNTLLQSMKN
Chicken_BMP10  MDSIVLQLWAGLCLLVHLATCSPILSLEHSSLEEGEPLFDEFLSEQDGVDFNTLLQNMKN
               *.*:** * * :** .: .: ***:.**:*.***. .:*.:..::****:*******.**:

Human_BMP10    EFLKTLNLSDIPTQDSAKVDPPEYMLELYNKFATDRTSMPSANIIRSFKNEDLFSQPVSF
Murine_BMP10   EFLKTLNLSDIPVQDTGRVDPPEYMLELYNKFATDRTSMPSANIIRSFKNEDLFSQPVTF
Chicken_BMP10  EFLKTLNLSDIPLHESAKVDPPEYMLELYNKFATDRTSMPSANIIRSFKNEDLASHPVGV
               ************ :.:.:****************************** *:** .

Human_BMP10    NGLRKYPLLFNVSIPHHEEVIMAELRLYTLVQRDRMIYDGVDRKITIFEVLE-SKGDNEG
Murine_BMP10   NGLRKYPLLFNVSIPHHEEVVMAELRLYTLVQRDRMMYDGVDRKITIFEVLE-SADGSEE
Chicken_BMP10  IGVRKYPLLFNVSIPHHEEITMAELRLYTLVERDQMLYEGLDRKVTIFEVLENDHMGVGE
               *:*************** :.**********:**:*:*:***:******  . .

Human_BMP10    ERNMLVLVSGEIYGTNSEWETFDVTDAIRRWQKSGSSTHQLEVHIESKHDEAEDASSGRL
Murine_BMP10   ERSMLVLVSTEIYGTNSEWETFDVTDATRRWQKSGPSTHQLEIHIESRQNQAEDTGRGQL
Chicken_BMP10  ERKIVALASRQIYGTSSEWESFEVTEAIRRWRPAGLTTHRLEVHIESREG--EEQNGEGKL
               **.::.*.* :****.****:*:**:*** :::* :**:**:****:..  *: . *:*

Human_BMP10    EIDTSAQNKHNPLLIVFSDDQSSD-KERKEELNEMISHEQLPELDNLGLDSFSSGPGEEA
Murine_BMP10   EIDMSAQNKHDPLLVVFSDDQSND-KEQKEELNELITHEQDLDLD---SDAFFSGPDEEA
Chicken_BMP10  DIDINSEAKHVPLLIVFSDDQSNDQKEEKQELNEMIDHEQLLDLENLEVGNFHGHPGEEA
               :**  .:: **.***:*******.* ** *:****:* *** :*:  . * . *.***

Human_BMP10    LLQMRSNIIYDSTARIRRNAKGNYCKRTPLYIDFKEIGWDSWIIAPPGYEAYECRGVCNY
Murine_BMP10   LLQMRSNMIDDSSARIRRNAKGNYCKKTPLYIDFKEIGWDSWIIAPPGYEAYECRGVCNY
Chicken_BMP10  LLQMRSNIIYDSTARIRRNAKGNYCKKTPLYIDFKEIGWDSWIIAPAGYEAYECHGVCAY
               *******:* **:************:******************.*******:***  *

Human_BMP10    PLAEHLTPTKHAIIQALVHLKNSQKASKACCVPTKLEPISILYLDKGVVTYKFKYEGMAV
Murine_BMP10   PLAEHLTPTKHAIIQALVHLKNSQKASKACCVPTKLDPISILYLDKGVVTYKFKYEGMAV
Chicken_BMP10  PLTEHVTPTKHAIVQTLVHLKNPQKASKACCVPTKLDPISILYMDAGVVTYKFKYEGMVV
               **:**:*******:*:******.************:*******:* *************.*

Human_BMP10    SECGCR (SEQ. ID. NO:4)
Murine_BMP10   SECGCR (SEQ. ID. NO:9)
Chicken_BMP10  SECGCR (SEQ. ID. NO:10)
               ******
```

FIGURE 2

Mature Human BMP-9 and BMP-10

```
bmp9     SAGAGSHCQK TSLRVNFEDI GWDSWIIAPK EYEAYECKGG CFFPLADDVT PTKHAIVQTL 60
bmp10    -NAKGNYCKR TPLYIDFKEI GWDSWIIAPP GYEAYECRGV CNYPLAEHLT PTKHAIIQAL 59
          .*.:*:: *.*  ::*:;* ******** *****:*  * ;***:.:* *****:*;* bmp9     VHLKFPTKVG KACCVPTKLS PISVLYKDDM GVPTLKYHYE GMSVAECGCR 110   (SEQ ID NO:3)
bmp10    VHLKNSQKAS KACCVPTKLE PISILYLD-K GVVTYKFKYE GMAVSECGCR 108   (SEQ ID NO:6)
         **** . *.. ********. ***:** *   ** * *:;** **:*:*****
```

FIGURE 3

METHODS AND COMPOSITIONS FOR INCREASING RED BLOOD CELLS

RELATED APPLICATIONS

This application is a continuation of U.S. application Ser. No. 16/422,117, filed May 24, 2019 (now allowed), which is a continuation of U.S. application Ser. No. 15/783,056, filed Oct. 13, 2017 (now U.S. Pat. No. 10,344,066), which is a continuation of U.S. application Ser. No. 13/827,477, filed Mar. 14, 2013 (now U.S. Pat. No. 9,809,636), which claims the benefit of priority to U.S. Provisional Application Ser. No. 61/621,154, filed Apr. 6, 2012. The specification of each of the foregoing applications is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Oct. 5, 2020, is named 1848179-062-104_Seq.txt and is 47,179 bytes in size.

BACKGROUND OF THE INVENTION

The mature red blood cell, or erythrocyte, is responsible for oxygen transport in the circulatory systems of vertebrates. Red blood cells contain high concentrations of hemoglobin, a protein that binds oxygen in the lungs at relatively high partial pressure of oxygen ($pO_2$) and delivers oxygen to areas of the body with a relatively low $pO_2$.

Mature red blood cells are produced from pluripotent hematopoietic stem cells in a process termed erythropoiesis. Postnatal erythropoiesis occurs primarily in the bone marrow and in the red pulp of the spleen. The coordinated action of various signaling pathways control the balance of cell proliferation, differentiation, survival and death. Under normal conditions, red blood cells are produced at a rate that maintains a constant red cell mass in the body, and production may increase or decrease in response to various stimuli, including increased or decreased oxygen tension or tissue demand. The process of erythropoiesis begins with the formation of lineage committed precursor cells and proceeds through a series of distinct precursor cell types. The final stages of erythropoiesis occur as reticulocytes are released into the bloodstream and lose their mitochondria and ribosomes while assuming the morphology of mature red blood cell. An elevated level of reticulocytes, or an elevated reticulocyte:erythrocyte ratio, in the blood is indicative of increased red blood cell production rates.

Erythropoietin (EPO) is widely recognized as the most significant positive regulator of postnatal erythropoiesis in vertebrates. EPO regulates the compensatory erythropoietic response to reduced tissue oxygen tension (hypoxia) and low red blood cell levels or low hemoglobin levels. In humans, elevated EPO levels promote red blood cell formation by stimulating the generation of erythroid progenitors in the bone marrow and spleen. In the mouse, EPO enhances erythropoiesis primarily in the spleen.

Anemia is a broadly-defined condition characterized by lower than normal levels of hemoglobin or red blood cells in the blood. In some instances, anemia is caused by a primary disorder in the production or survival of red blood cells. More commonly, anemia is secondary to diseases of other systems (Weatherall & Provan (2000) Lancet 355, 1169-1175). Anemia may result from a reduced rate of production or increased rate of destruction of red blood cells or by loss of red blood cells due to bleeding. Anemia may result from a variety of disorders that include, for example, chronic renal failure, chemotherapy treatment, myelodysplastic syndrome, rheumatoid arthritis, and bone marrow transplantation.

Treatment with EPO typically causes a rise in hemoglobins by about 1-3 g/dL in healthy humans over a period of weeks. When administered to anemic individuals, this treatment regimen often provides substantial increases in hemoglobin and red blood cell levels and leads to improvements in quality of life and prolonged survival. EPO is not uniformly effective, and many individuals are refractory to even high doses (Horl et al. (2000) Nephrol Dial Transplant 15, 43-50). Over 50% of patients with cancer have an inadequate response to EPO, approximately 10% with end-stage renal disease are hyporesponsive (Glaspy et al. (1997) J Clin Oncol 15, 1218-1234; Demetri et al. (1998) J Clin Oncol 16, 3412-3425), and less than 10% with myelodysplastic syndrome respond favorably (Estey (2003) Curr Opin Hematol 10, 60-67). Several factors, including inflammation, iron and vitamin deficiency, inadequate dialysis, aluminum toxicity, and hyperparathyroidism may predict a poor therapeutic response. The molecular mechanisms of resistance to EPO are as yet unclear. Recent evidence suggests that higher doses of EPO may be associated with an increased risk of cardiovascular morbidity, tumor growth, and mortality in some patient populations (Krapf et al., 2009, Clin J Am Soc Nephrol 4:470-480; Glaspy, 2009, Annu Rev Med 60:181-192). It has therefore been recommended that EPO-based therapeutic compounds (erythropoietin-stimulating agents, ESAs) be administered at the lowest dose sufficient to avoid the need for red blood cell transfusions (Jelkmann et al., 2008, Crit Rev Oncol. Hematol 67:39-61).

Thus, it is an object of the present disclosure to provide alternative methods and compositions for increasing red blood cell levels in patients.

SUMMARY OF THE INVENTION

In part, the disclosure demonstrates that BMP9 polypeptides or BMP10 polypeptides may be used to increase red blood cell and hemoglobin levels. In particular, the disclosure demonstrates that BMP9, when administered in vivo, causes a profound and rapid increase in red blood cell levels, hematocrit and hemoglobin. BMP10 is closely related to BMP9 and is known to signal through the same set of receptors. Therefore, in certain embodiments, the disclosure provides methods for using BMP9 or BMP10 polypeptides (or a combination thereof) to increase red blood cell and hemoglobin levels in patients and to treat disorders associated with low red blood cell or hemoglobin levels in patients in need thereof.

In certain aspects, the present disclosure provides BMP9 polypeptides. In certain embodiments, a BMP9 polypeptide has an amino acid sequence that comprises, consists of, or consists essentially of, the amino acid sequence of SEQ ID NO: 1, 2, 3, 7, 8 or 16, or an amino acid sequence that is at least 63%, 70%, 75%, 80%, 85%, 90%, 95%, 97%, 98%, or 99% identical to any of the foregoing. A BMP9 polypeptide may comprise an amino acid sequence that is encoded by a nucleic acid of SEQ ID NO:11, including any portion thereof, such as nucleotides 1121-1450 that encode the mature portion of BMP9, and a BMP9 polypeptide may be encoded by a nucleic acid that hybridizes to a nucleic acid that is complementary to the sequence of nucleotides 1121-

1450 of SEQ ID NO:11 under less stringent, moderately stringent or highly stringent hybridization conditions.

In certain aspects, the present disclosure provides BMP10 polypeptides. In certain embodiments, a BMP10 polypeptide has an amino acid sequence that comprises, consists of, or consists essentially of, the amino acid sequence of SEQ ID NO: 4, 5, 6, 9, 10 or 17, or an amino acid sequence that is at least 63%, 70%, 75%, 80%, 85%, 90%, 95%, 97%, 98%, or 99% identical to any of the foregoing. A BMP10 polypeptide may comprise an amino acid sequence that is encoded by a nucleic acid of SEQ ID NO:12, including any portion thereof, such as nucleotides 1108-1431 that encode the mature portion of BMP10, and a BMP10 polypeptide may be encoded by a nucleic that hybridizes to a nucleic acid that is complementary to the sequence of nucleotides 1108-1431 of SEQ ID NO:12 under less stringent, moderately stringent or highly stringent hybridization conditions.

In certain aspects, the disclosure provides pharmaceutical preparations comprising a BMP9 or BMP10 polypeptide and a pharmaceutically acceptable carrier. The BMP9 or BMP10 polypeptide may bind to one or more type I (e.g., ALK1, ALK2) or type II (e.g., ActRIIA, ActRIIB, BMPRII) receptors with a Kd less than 10 micromolar, less than 1 micromolar, less than 100 nanomolar, less than 10 nanomolar, or less than 1 nanomolar. Typically, a BMP9 or BMP10 polypeptide will bind to both a type I receptor and a type II receptor, although binding to one of the receptors may be at a very weak affinity. Optionally, the BMP9 or BMP10 polypeptide will stimulate expression from a SMAD1- or SMAD5-responsive promoter in a cell, such as a promoter containing the BMP-responsive element (BRE) from the ID1 gene.

A pharmaceutical preparation may further comprise a BMP9 prodomain polypeptide or a BMP10 prodomain polypeptide. In certain embodiments, a BMP9 prodomain polypeptide has an amino acid sequence that comprises, consists of, or consists essentially of, the amino acid sequence of 23-319 of SEQ ID NO: 1 or an amino acid sequence that is at least 63%, 70%, 75%, 80%, 85%, 90%, 95%, 97%, 98%, or 99% identical to same. A BMP9 prodomain polypeptide may comprise an amino acid sequence that is encoded by the sequence of nucleotides 230-1120 of SEQ ID NO:11, including any portion thereof, and a BMP9 prodomain polypeptide may be encoded by a nucleic acid that hybridizes to a nucleic acid that is complementary to the sequence of nucleotides 230-1120 of SEQ ID NO:11 under less stringent, moderately stringent or highly stringent hybridization conditions. In certain embodiments, a BMP10 prodomain polypeptide has an amino acid sequence that comprises, consists of, or consists essentially of, the amino acid sequence of 22-316 of SEQ ID NO: 4 or an amino acid sequence that is at least 63%, 70%, 75%, 80%, 85%, 90%, 95%, 97%, 98%, or 99% identical to same. A BMP10 prodomain polypeptide may comprise an amino acid sequence that is encoded by the sequence of nucleotides 223-1107 of SEQ ID NO:12, including any portion thereof, and a BMP10 prodomain polypeptide may be encoded by a nucleic acid that hybridizes to a nucleic acid that is complementary to the sequence of nucleotides 223-1107 of SEQ ID NO:12 under less stringent, moderately stringent or highly stringent hybridization conditions. A prodomain polypeptide may be covalently or non-covalently associated with a BMP9 or BMP10 polypeptide.

Preferably, a pharmaceutical preparation is substantially pyrogen free. In general, it is preferable that a BMP9 or BMP10 polypeptide be expressed in a mammalian cell line that mediates suitably natural glycosylation so as to diminish the likelihood of an unfavorable immune response in a patient. Human and CHO cell lines have been used successfully, and it is expected that other common mammalian expression vectors will be useful.

In certain aspects, the disclosure provides methods for making a BMP9 or BMP10 polypeptide. Such a method may include expressing any of the nucleic acids (e.g., SEQ ID NO: 11 or 12) disclosed herein in a suitable cell, such as a Chinese hamster ovary (CHO) cell. Such a method may comprise: a) culturing a cell under conditions suitable for expression of the BMP9 or BMP10 polypeptide, wherein said cell is transformed with a BMP9 or BMP10 expression construct; and b) recovering the BMP9 or BMP10 polypeptide so expressed. BMP9 or BMP10 polypeptides may be recovered as crude, partially purified or highly purified fractions using any of the well known techniques for obtaining protein from cell cultures. Purification may be achieved by contacting the BMP9 or BMP10 polypeptide with a ligand binding domain of a receptor protein, such as ALK1, ALK2, ActrIIA, ActRIIB or BMPRII or modified version thereof that binds to BMP9 or BMP10. The ligand binding domain may, for example, be used as a fusion with an Fc portion of an IgG (optionally with an intervening linker) and immobilized on a protein A-coated surface.

In certain aspects, a BMP9 or BMP10 polypeptide, or a pharmaceutical preparation comprising one or more of the foregoing, may be used in a method for promoting red blood cell production or increasing red blood cell levels in a subject. In certain embodiments, the disclosure provides methods for treating a disorder associated with low red blood cell counts or low hemoglobin levels (e.g., an anemia), or to promote red blood cell production, in patients in need thereof. A method may comprise administering to a subject in need thereof an effective amount of a BMP9 or BMP10 polypeptide. In certain aspects, the disclosure provides uses of BMP9 or BMP10 polypeptides for making a medicament for the treatment of a disorder or condition as described herein.

BRIEF DESCRIPTION OF THE DRAWINGS

FIG. 1 shows a multiple sequence alignment of human, murine and chicken BMP9 proteins. The alignment was obtained using the Clustal W program.

FIG. 2 shows a multiple sequence alignment of human, murine and chicken BMP10 proteins. The alignment was obtained using the Clustal W program.

FIG. 3 shows an alignment of the mature portions of BMP9 and BMP10.

DETAILED DESCRIPTION OF THE INVENTION

1. Overview

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Bone morphogenetic protein 9 (BMP9) and BMP10 are two closely related members of the TGF-beta superfamily. These proteins are thought to be produced as disulfide linked homodimers that can circulate in the blood. BMP signals are mediated by heteromeric complexes of type I and type II serine/threonine kinase receptors, which phosphorylate and activate downstream Smad proteins upon ligand stimulation (Massague, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling. Type II receptors are required for binding ligands and for expression of Type I receptors. Type I and II activin receptors form a stable complex after ligand binding, resulting in phosphorylation of Type I receptors by Type II receptors. BMP9 and BMP10 are thought to signal through the Type I receptors ALK1 and ALK2 and the Type II receptors ActRIIA, ActRIIB and BMPRII.

As demonstrated herein, a BMP9 polypeptide (and, as inferred by homology and common signaling pathway, a BMP10 polypeptide) is effective at increasing red blood cell levels in vivo and is expected to have beneficial effects in a variety of models for anemias. It should be noted that hematopoiesis is a complex process, regulated by a variety of factors, including erythropoietin, G-CSF and iron homeostasis. The terms "increase red blood cell levels" and "promote red blood cell formation" refer to clinically observable metrics, such as hematocrit, red blood cell counts and hemoglobin measurements, and are intended to be neutral as to the mechanism by which such changes occur.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. BMP9 and BMP10 Polypeptides and Nucleic Acids

In certain aspects, the invention relates to BMP9 polypeptides and BMP10 polypeptides, including, for example, mature human BMP9 and BMP10 proteins as well as BMP9 or BMP10 polypeptides that retain the prodomain, whether covalently or non-covalently attached, and variants and truncations of the foregoing. Such variations and truncations may be selected to retain the ability to stimulate signaling by one or more of the known receptors for BMP9 or BMP10, including ALK1, ALK2, ActRIIA, BMPR2 and ActRIIB Optionally, a BMP9 or BMP10 polypeptide can increase expression of luciferase in a cell line transfected with a BRE-luciferase reporter gene construct.

As used herein, the terms "BMP-9" or "BMP-10" refer to the family of BMP-9 or BMP-10 proteins, respectively, from any species and variants derived from such proteins by mutagenesis, truncation or other modification. BMP-9 proteins and BMP-10 proteins are well-conserved across vertebrate lineages, particularly in the mature portion of the protein, as shown in FIGS. 1 and 2. The mature portions of human BMP-9 and BMP-10 also show substantial identity to each other (64%) (FIG. 3). Members of the BMP-9 or BMP-10 families are generally secreted proteins, composed of a signal peptide, a pro-domain that binds to the mature portion in a manner that competes with binding to type II receptors (e.g., BMPR2, ActRIIA, ActRIIB) and a mature portion containing a cysteine knot. The mature portion binds to both a type I receptor (e.g., ALK1 or ALK2) and a type II receptor (e.g., BMPR2, ActRIIA or ActRIIB) to form a signaling complex.

The term "BMP9 polypeptide" includes polypeptides comprising any naturally occurring polypeptide of a BMP-9 family member, respectively, as well as any variants thereof (including mutants, fragments, fusions, and peptidomimetic forms) that retain a useful activity. For example, BMP9 polypeptides may comprise polypeptides derived from the sequence of any known BMP9 protein and may include forms expressed with a signal peptide, as a proprotein form (containing both the prodomain and the mature portion) and as the fully mature form. As shown in FIG. 1, vertebrates as diverse as humans, mice and chickens have highly conserved BMP9 proteins, and therefore functional variants may, for example, be selected by reference to amino acids that are less conserved among different vertebrate species as such changes will generally be tolerated. BMP9 polypeptides may comprise, consist essentially of, or consist of, an amino acid sequence that is at least 63%, 70%, 75%, 80%, 85%, 90%, 95%, 97%, 98%, 99%, or 100% identical to the sequence of a naturally occurring BMP9 polypeptide such as any of SEQ. ID. Nos. 1, 2, 3, 7 or 8 or the mature portions of SEQ. ID. Nos. 7 or 8. Numbering of amino acids for all human BMP9 polypeptides described herein is based on the numbering for SEQ ID NO:1, unless specifically designated otherwise.

Examples of BMP9 polypeptides include:

Full-length human BMP9 precursor (including signal sequence, corresponding to amino acids 1-22) (Genbank NP_057288):

```
                                                            (SEQ. ID. NO: 1)
  1  MCPGALWVAL  PLLSLLAGSL  QGKPLQSWGR  GSAGGNAHSP  LGVPGGGLPE  HTFNLKMFLE

61  NVKVDFLRSL  NLSGVPSQDK  TRVEPPQYMI  DLYNRYTSDK  STTPASNIVR  SFSMEDAISI

121  TATEDFPFQK  HILLFNISIP  RHEQITRAEL  RLYVSCQNHV  DPSHDLKGSV  VIYDVLDGTD

181  AWDSATETKT  FLVSQDIQDE  GWETLEVSSA  VKRWVRSDST  KSKNKLEVTV  ESHRKGCDTL

241  DISVPPGSRN  LPFFVVFSND  HSSGTKETRL  ELREMISHEQ  ESVLKKLSKD  GSTEAGESSH

301  EEDTDGHVAA  GSTLARRKRS  AGAGSHCQKT  SLRVNFEDIG  WDSWIIAPKE  YEAYECKGGC

361  FFPLADDVTP  TKHAIVQTLV  HLKFPTKVGK  ACCVPTKLSP  ISVLYKDDMG  VPTLKYHYEG

421  MSVAECGCR
```

Full-length human BMP9 proprotein (signal sequence removed but including pro-domain, corresponding to amino acids 23-429 of SEQ ID NO:1):

```
                                   (SEQ. ID. NO: 2)
KPLQSWGRGS  AGGNAHSPLG  VPGGGLPEHT  FNLKMFLENV

KVDFLRSLNL  SGVPSQDKTR  VEPPQYMIDL  YNRYTSDKST

TPASNIVRSF  SMEDAISITA  TEDFPFQKHI  LLFNISIPRH

EQITRAELRL  YVSCQNHVDP  SHDLKGSVVI  YDVLDGTDAW

DSATETKTFL  VSQDIQDEGW  ETLEVSSAVK  RWVRSDSTKS

KNKLEVTVES  HRKGCDTLDI  SVPPGSRNLP  FFVVESNDHS

SGTKETRLEL  REMISHEQES  VLKKLSKDGS  TEAGESSHEE

DTDGHVAAGS  TLARRKRSAG  AGSHCQKTSL  RVNFEDIGWD

SWIIAPKEYE  AYECKGGCFF  PLADDVTPTK  HAIVQTLVHL

KFPTKVGKAC  CVPTKLSPIS  VLYKDDMGVP  TLKYHYEGMS

VAECGCR
```

Mature human BMP9 (both signal sequence and pro-domain removed, corresponding to amino acids 320-429 of SEQ ID NO:1):

```
                                             (SEQ. ID. NO: 3)
SAGAGSHCQK  TSLRVNFEDI  GWDSWIIAPK  EYEAYECKGG

CFFPLADDVT  PTKHAIVQTL  VHLKFPTKVG  KACCVPTKLS

PISVLYKDDM  GVPTLKYHYE  GMSVAECGCR
```

The term "BMP10 polypeptide" includes polypeptides comprising any naturally occurring polypeptide of a BMP10 family member, respectively, as well as any variants thereof (including mutants, fragments, fusions, and peptidomimetic forms) that retain a useful activity. For example, BMP10 polypeptides may comprise polypeptides derived from the sequence of any known BMP10 protein and may include forms expressed with a signal peptide, as a proprotein form and as the fully mature form. As shown in FIG. 2, vertebrates as diverse as humans, mice and chickens have highly conserved BMP10 proteins, and therefore functional variants may, for example, be selected by reference to amino acids that are less conserved among different vertebrate species. BMP10 polypeptides may comprise, consist essentially of, or consist of, an amino acid sequence that is at least 63%, 70%, 75%, 80%, 85%, 90%, 95%, 97%, 98%, 99%, or 100% identical to the sequence of a naturally occurring BMP10 polypeptide such as any of SEQ. ID. Nos. 4, 5, 6, 9 or 10 or the mature portions of SEQ. ID. Nos. 9 or 10. Numbering of amino acids for all human BMP10 polypeptides described herein is based on the numbering for SEQ ID NO:4, unless specifically designated otherwise.

Examples of BMP10 polypeptides include:

Full-length human BMP10 precursor (including signal sequence, corresponding to amino acids 1-21) (Genbank NP_055297):

```
                                                            (SEQ. ID. NO: 4)
  1  MGSLVLTLCA  LFCLAAYLVS  GSPIMNLEQS  PLEEDMSLFG  DVFSEQDGVD  FNTLLQSMKD

61  EFLKTLNLSD  IPTQDSAKVD  PPEYMLELYN  KFATDRTSMP  SANIIRSFKN  EDLFSQPVSF

121  NGLRKYPLLF  NVSIPHHEEV  IMAELRLYTL  VQRDRMIYDG  VDRKITIFEV  LESKGDNEGE

181  RNMLVLVSGE  IYGTNSEWET  FDVTDAIRRW  QKSGSSTHQL  EVHIESKHDE  AEDASSGRLE

241  IDTSAQNKHN  PLLIVFSDDQ  SSDKERKEEL  NEMISHEQLP  ELDNLGLDSF  SSGPGEEALL

301  QMRSNIIYDS  TARIRRNAKG  NYCKRTPLYI  DFKEIGWDSW  IIAPPGYEAY  ECRGVCNYPL

361  AEHLTPTKHA  IIQALVHLKN  SQKASKACCV  PTKLEPISIL  YLDKGVVTYK  FKYEGMAVSE

421  CGCR
```

Full-length human BMP10 proprotein (signal sequence removed but including pro-domain, corresponding to amino acids 22-424 of SEQ ID NO:4):

(SEQ. ID. NO: 5)
```
SPIMNLEQSP LEEDMSLFGD VFSEQDGVDF NTLLQSMKDE

FLKTLNLSDI PTQDSAKVDP PEYMLELYNK FATDRTSMPS

ANIIRSFKNE DLFSQPVSFN GLRKYPLLFN VSIPHHEEVI

MAELRLYTLV QRDRMIYDGV DRKITIFEVL ESKGDNEGER

NMLVLVSGEI YGTNSEWETF DVTDAIRRWQ KSGSSTHQLE

VHIESKHDEA EDASSGRLEI DTSAQNKHNP LLIVFSDDQS

SDKERKEELN EMISHEQLPE LDNLGLDSFS SGPGEEALLQ

MRSNIIYDST ARIRRNAKGN YCKRTPLYID FKEIGWDSWI

IAPPGYEAYE CRGVCNYPLA EHLTPTKHAI IQALVHLKNS

QKASKACCVP TKLEPISILY LDKGVVTYKF KYEGMAVSEC

GCR
```

Mature human BMP10 (both signal sequence and pro-domain removed, corresponding to amino acids 317-424 of SEQ ID NO:4):

(SEQ ID NO: 6)
```
NAKGNYCKRT PLYIDFKEIG WDSWIIAPPG YEAYECRGVC

NYPLAEHLTP TKHAIIQALV HLKNSQKASK ACCVPTKLEP

ISILYLDKGV VTYKFKYEGM AVSECGCR
```

In certain aspects, the disclosure provides isolated and/or recombinant nucleic acids encoding any of the BMP9 or BMP10 polypeptides disclosed herein. Such nucleic acids may be DNA or RNA molecules. These nucleic acids may be used, for example, in methods for making BMP9 or BMP10 polypeptides or as direct therapeutic agents (e.g., in a gene therapy approach).

A nucleic acid sequence encoding a human BMP9 precursor protein is as follows: (Genbank NM_016204)

(SEQ. ID. NO: 11)
```
   1 cggtccagcc cggcagcggg tgagagtggg tgctggccag gacggttcct tcagagcaaa
  61 cagcagggag atgccggccc gctccttccc agctcctccc cgtgcccgct aacacagcac
 121 ggccgcctgc agtctcctct ctgggtgatt gcgcgggcct aagatgtgtc ctggggcact
 181 gtgggtggcc ctgcccctgc tgtccctgct ggctggctcc ctacagggga agccactgca
 241 gagctgggga cgagggtctg ctgggggaaa cgcccacagc ccactggggg tgcctggagg
 301 tgggctgcct gagcacacct tcaacctgaa gatgtttctg gagaacgtga aggtggattt
 361 cctgcgcagc cttaacctga gtggggtccc ttcgcaggac aaaaccaggg tggagccgcc
 421 gcagtacatg attgacctgt acaacaggta cacgtccgat aagtcgacta cgccagcgtc
 481 caacattgtg cggagcttca gcatggaaga tgccatctcc ataactgcca cagaggactt
 541 cccccttccag aagcacatct tgctcttcaa catctccatt cctaggcatg agcagatcac
 601 cagagctgag ctccgactct atgtctcctg tcaaaatcac gtggacccct ctcatgacct
 661 gaaaggaagc gtggtcattt atgatgttct ggatggaaca gatgcctggg atagtgctac
 721 agagaccaag accttcctgg tgtcccagga cattcaggat gagggctggg agaccttgga
 781 agtgtccagc gccgtgaagc gctgggtccg gtccgactcc accaagagca aaaataagct
 841 ggaagtgact gtggagagcc acaggaaggg ctgcgacacg ctggacatca gtgtcccccc
 901 aggttccaga aacctgccct tctttgttgt cttctccaat gaccacagca gtgggaccaa
 961 ggagaccagg ctggagctga gggagatgat cagccatgaa caagagagcg tgctcaagaa
1021 gctgtccaag gacggctcca cagaggcagg tgagagcagt cacgaggagg acacggatgg
1081 ccacgtggct gcggggtcga ctttagccag gcggaaaagg agcgccgggg ctggcagcca
1141 ctgtcaaaag acctccctgc gggtaaactt cgaggacatc ggctgggaca gctggatcat
1201 tgcacccaag gagtatgaag cctacgagtg taagggcggc tgcttcttcc ccttggctga
1261 cgatgtgacg ccgacgaaac acgctatcgt gcagacccct gtgcatctca agttcccac
1321 aaaggtgggc aaggcctgct gtgtgcccac caaactgagc cccatctccg tcctctacaa
1381 ggatgacatg ggggtgccca ccctcaagta ccattacgag ggcatgagcg tggcagagtg
1441 tgggtgcagg tag
```

The coding region for BMP9 (signal peptide, prodomain and mature portion) runs from position 164-1453 of SEQ. ID. No. 11. The signal peptide is encoded by nucleotides 164-229, the prodomain by nucleotides 230-1120 and the mature peptide by positions 1121-1450.

The nucleic acid sequence encoding a human BMP10 precursor protein is as follows (Genbank NM_014482):

```
                                                       (SEQ. ID. NO: 12)
   1   ggggagagga agagtggtag ggggagggag agagagagga agagtttcca aacttgtctc
  61   cagtgacagg agacatttac gttccacaag ataaaactgc cacttagagc ccagggaagc
 121   taaaccttcc tggcttggcc taggagctcg agcggagtca tgggctctct ggtcctgaca
 181   ctgtgcgctc ttttctgcct ggcagcttac ttggtttctg gcagccccat catgaaccta
 241   gagcagtctc ctctggaaga agatatgtcc ctctttggtg atgttttctc agagcaagac
 301   ggtgtcgact ttaacacact gctccagagc atgaaggatg agtttcttaa gacactaaac
 361   ctctctgaca tccccacgca ggattcagcc aaggtggacc caccagagta catgttggaa
 421   ctctacaaca aatttgcaac agatcggacc tccatgccct ctgccaacat cattaggagt
 481   ttcaagaatg aagatctgtt tccccagccg gtcagtttta atgggctccg aaaatacccc
 541   ctcctcttca atgtgtccat tcctcaccat gaagaggtca tcatggctga acttaggcta
 601   tacacactgg tgcaaaggga tcgtatgata tacgatggag tagaccggaa aattaccatt
 661   tttgaagtgc tggagagcaa aggggataat gagggagaaa gaaacatgct ggtcttggtg
 721   tctggggaga tatatggaac caacagtgag tgggagactt tgatgtcac agatgccatc
 781   agacgttggc aaaagtcagg ctcatccacc caccagctgg aggtccacat tgagagcaaa
 841   cacgatgaag ctgaggatgc cagcagtgga cggctagaaa tagataccag tgcccagaat
 901   aagcataacc ctttgctcat cgtgttttct gatgaccaaa gcagtgacaa ggagaggaag
 961   gaggaactga atgaaatgat tccccatgag caacttccag agctggacaa cttgggcctg
1021   gatagctttt ccagtgacc tggggaagag gctttgttgc agatgagatc aaacatcatc
1081   tatgactcca ctgcccgaat cagaaggaac gccaaaggaa actactgtaa gaggacccccg
1141   ctctacatcg acttcaagga gattgggtgg gactcctgga tcatcgctcc gcctggatac
1201   gaagcctatg aatgccgtgg tgtttgtaac taccccctgg cagagcatct cacacccaca
1261   aagcatgcaa ttatccaggc cttggtccac ctcaagaatt cccagaaagc ttccaaagcc
1321   tgctgtgtgc ccacaaagct agagcccatc tccatcctct atttagacaa aggcgtcgtc
1381   acctacaagt ttaaatacga aggcatggcc gtctccgaat gtggctgtag atagaagaag
1441   agtcctatgg cttatttaat aactgtaaat gtgtatattt ggtgttccta tttaatgaga
1501   ttatttaata agggtgtaca gtaatagagg cttgctgcct tcaggaaatg gacaggtcag
1561   tttgttgtag gaaatgcata tttt
```

The coding region for BMP10 (signal peptide, prodomain and mature portion) runs from position 160-1434 of SEQ. ID. No. 12. The signal peptide is encoded by nucleotides 160-222, the prodomain by nucleotides 223-1107 and the mature peptide by positions 1108-1431.

In certain aspects, the subject nucleic acids encoding BMP9 or BMP10 polypeptides are further understood to include nucleic acids that are variants of SEQ ID NOs: 11 or 12. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 11 or 12.

In certain embodiments, the disclosure provides isolated or recombinant nucleic acid sequences that are at least 63%, 70%. 80%, 85%, 90%, 95%, 97%, 98%, 99% or 100% identical to SEQ ID NO: 11 or 12 or the portions thereof that encode the prodomain or mature portion. One of ordinary skill in the art will appreciate that nucleic acid sequences complementary to SEQ ID NO: 11 or 12, and variants of SEQ ID NO: 11 or 12, are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under stringent conditions to the nucleotide sequence designated in SEQ ID NO: 11 or 12, including the portions thereof that encode the prodomain or mature portion, complement sequence of SEQ ID NO: 11 or 12, including the portions thereof that encode the prodomain or mature portion thereof. In a particular embodiment, the disclosure provides nucleic acids that hybridize under stringent conditions to a complement to the nucleic acid of 1121-1450 of SEQ ID NO:11 or a complement of the nucleic acid of 1108-1431 of SEQ ID NO:12, and BMP9 or BMP10 polypeptides encoded by the foregoing. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NO: 11 or 12 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. In certain embodiments, the BMP9 or BMP10 polypeptide will be encoded by an alternative nucleotide sequence. Alternative nucleotide sequences are degenerate with respect to the native BMP9 or BMP10 nucleic acid sequence but still encode for the same fusion protein.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the disclosure, the subject nucleic acid is provided in an expression vector comprising a nucleotide sequence encoding a BMP9 or BMP10 polypeptide and operably linked to at least one regulatory sequence. Regulatory sequences are art-recognized and are selected to direct expression of the BMP9 or BMP10 polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a BMP9 or BMP10 polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid for production of BMP9 or BMP10 polypeptides can be produced by ligating the cloned gene, or a portion thereof, into a vector suitable for expression in either prokaryotic cells, eukaryotic cells (yeast, avian, insect or mammalian), or both. Expression vehicles for production of a recombinant BMP9 or BMP10 polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject BMP9 or BMP10 polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject BMP9 or BMP10 polypeptides in cells propagated in culture, e.g., to produce proteins, including fusion proteins or variant proteins, for purification.

This disclosure also pertains to a host cell transfected with a recombinant gene including a coding sequence for one or more of the subject BMP9 or BMP10 polypeptides. The host cell may be any prokaryotic or eukaryotic cell. For example, a BMP9 or BMP10 polypeptide of the invention may be expressed in bacterial cells such as E. coli, insect cells (e.g., using a baculovirus expression system), yeast, or mammalian cells. Other suitable host cells are known to those skilled in the art.

The above-described nucleic acids may be used to express BMP9 or BMP10 polypeptides in suitable cells, including, for example, HEK cells, COS cells and CHO cells. The signal sequence can be a native signal sequence of BMP9 or BMP10, or a signal sequence from another protein, such as a tissue plasminogen activator (TPA) signal sequence or a honey bee melittin (HBM) signal sequence. The prodomain sequences of BMP9 and BMP10 may be interchanged, such that a BMP10 mature portion is expressed with a BMP9 prodomain or vice versa. The protein PACE (or Furin) mediates cleavage of the proprotein into two peptides, the proprotein and the mature portion, and thus it is useful to express a PACE transgene in a cell that is intended to produce a BMP9 or BMP10 polypeptide if such cleavage is desired. It is generally accepted that members of the GDF or BMP families need to dissociate from their prodomains in order to become fully active. In the case of BMP9 or BMP10, the prodomain remains associated with the mature portion, thus it may be desirable to separate the mature portion to generate the administrable pharmaceutical form. Alternatively, it is recognized here that the prodomain may confer desirable pharmaceutical properties, including, for example, longer serum half-life and greater bioavailability, and thus in certain embodiments the disclosure provides pharmaceutical preparations comprising the mature portion of a BMP9 or BMP10 polypeptide that is covalently or non-covalently associated with a prodomain polypeptide. A "prodomain polypeptide" is a polypeptide comprising, consisting essentially of, or consisting of, an amino acid sequence that is at least 63%, 70%, 75%, 80%, 85%, 90%, 95%, 97%, 98%, 99%, or 100% identical to the sequence of a naturally occurring BMP9 or BMP10 prodomain such as amino acids 23-319 of SEQ ID No. 1 or amino acids 22-316 of SEQ ID No. 4. It will be apparent that a prodomain polypeptide should not generally include more than 30, 20, 10 or 5 amino acids of the corresponding mature portion. In certain embodiments, a prodomain polypeptide will bind to the mature portion of a BMP9 or BMP10 polypeptide with a KD of no greater than $10^{-6}$M, $10^{-7}$M, $10^{-8}$M or $10^{-9}$M, or less.

In certain embodiments, the present disclosure contemplates making functional variants by modifying the structure of a BMP9 or BMP10 polypeptide for such purposes as enhancing therapeutic efficacy, or stability (e.g., ex vivo shelf life and resistance to proteolytic degradation in vivo). BMP9 or BMP10 polypeptides can also be generated by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a BMP9 or BMP10 polypeptide results in a functional variant can be readily determined by assessing the ability of the BMP9 or BMP10 polypeptide to produce a response in cells relative to the unmodified BMP9 or BMP10 polypeptide, or to bind to one or more receptors. In the case of variations in a prodomain polypeptide, the functional activity of a variant may be assessed by measuring the ability of the prodomain to bind to a mature BMP9 or BMP10 polypeptide.

In certain embodiments, the present invention contemplates BMP9 or BMP10 polypeptides having specific mutations so as to alter the glycosylation of the BMP9 or BMP10 polypeptide. Alterations in amino acid sequence may be made so as to introduce one or more N-linked glycosylation sites, which are generally an NXS or NXT sequence. Mutations may also be selected so as to eliminate one or more glycosylation sites, such as O-linked or N-linked glycosylation sites. The alteration may also be made by the addition of, or substitution by, one or more asparagine, serine or threonine residues to the sequence of a BMP9 or BMP10 polypeptide. A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a BMP9 or BMP10 polypeptide is by chemical or enzymatic coupling of glycosides to the BMP9 or BMP10 polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 and in Aplin and Wriston (1981) CRC Crit. Rev. Biochem., pp. 259-306, incorporated by reference herein. Removal of one or more carbohydrate moieties present on a BMP9 or BMP10 polypeptide may be accomplished chemically and/or enzymatically. Chemical deglycosylation may involve, for example, exposure of the BMP9 or BMP10 polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on BMP9 or BMP10 polypeptides can be achieved by the use of a variety of endo- and exo-glycosidases as described by Thotakura et al. (1987) Meth. Enzymol. 138:350. The sequence of a BMP9 or BMP10 polypeptide may be adjusted, as appropriate, depending on the type of expression system used, as mammalian, yeast, insect and plant cells may all introduce differing glycosylation patterns that can be affected by the amino acid sequence of the peptide. In general, BMP9 or BMP10 polypeptides for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of a BMP9 or BMP10 polypeptide, including, optionally, truncation variants; pools of combinatorial mutants are especially useful for identifying BMP9 or BMP10 sequences. The purpose of screening such combinatorial libraries may be to generate, for example, BMP9 or BMP10 polypeptide variants which have altered properties, such as altered pharmacokinetics, or altered receptor binding. A variety of screening assays are provided below, and such assays may be used to evaluate variants. For example, a BMP9 or BMP10 polypeptide variant may be screened for the ability to bind to an ALK1, ActRIIA or ActRIIB polypeptide.

The activity of a BMP9 or BMP10 polypeptide or its variants may also be tested in a cell-based or in vivo assay. For example, the effect of a BMP9 or BMP10 polypeptide variant on the expression of genes involved in hematopoiesis may be assessed. Likewise, a BMP9 or BMP10 polypeptide may be administered to a mouse or other animal, and one or more blood measurements, such as an RBC count, hemoglobin levels, hematocrit levels, iron stores, or reticulocyte count may be assessed using art recognized methods. The BMP-responsive element (BRE) element, generally obtained from the promoter region of the ID1 gene is widely recognized as an appropriate reporter gene for members of the BMP/GDF family that stimulate SMAD 1/5/8 signaling. See, e.g., Logeart-Avramoglou D, et al., Anal Biochem. 2006 Feb. 1; 349(1):78-86. BMP9 or BMP10 polypeptide may also be measured by induction of alkaline phosphatase by ATDC5 mouse chondrogenic cells or MC3T3-E1 mouse osteoblastic cells. Nakamura, K. et al. (1999) Exp. Cell Res. 250:351.

In certain embodiments, the BMP9 or BMP10 polypeptides may further comprise post-translational modifications in addition to any that are naturally present in the BMP9 or BMP10 polypeptides. Such modifications include, but are not limited to, acetylation, carboxylation, glycosylation, phosphorylation, lipidation, acylation and modification with polyethylene glycol (PEG). As a result, BMP9 or BMP10 polypeptides may contain non-amino acid elements, such as polyethylene glycols, lipids, poly- or mono-saccharide, and phosphates. Effects of such non-amino acid elements on the functionality of a BMP9 or BMP10polypeptide may be tested as described herein for other BMP9 or BMP10 polypeptide variants. When a BMP9 or BMP10 polypeptide is produced in cells by cleaving a nascent form of BMP9 or BMP10 polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the BMP9 or BMP10 polypeptides.

In certain aspects, BMP9 or BMP10 polypeptides include fusion proteins having at least a portion of a BMP9 or BMP10 polypeptide and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$ (SEQ ID NO: 13)) fusion partners. As another example, a fusion domain may be selected so as to facilitate detection of the BMP9 or BMP10 polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a BMP9 or BMP10 polypeptide is fused with a domain that stabilizes the BMP9 or BMP10 polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further increasing red blood cell levels).

It is understood that different elements of the fusion proteins may be arranged in any manner that is consistent with the desired functionality. For example, a BMP9 or BMP10 polypeptide may be placed C-terminal to a heterologous domain, or, alternatively, a heterologous domain may be placed C-terminal to a BMP9 or BMP10 polypeptide. The BMP9 or BMP10 polypeptide domain and the heterologous domain need not be adjacent in a fusion protein, and additional domains or amino acid sequences may be included C- or N-terminal to either domain or between the domains.

In certain embodiments, the present invention makes available isolated and/or purified forms of the BMP9 or BMP10 polypeptides, which are isolated from, or otherwise substantially free of, other proteins.

In certain embodiments, BMP9 or BMP10 polypeptides (unmodified or modified) of the invention can be produced by a variety of art-known techniques. For example, polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the BMP9 or BMP10 polypeptides, fragments or variants thereof may be recombinantly produced using various expression systems (e.g., E. coli, Chinese Hamster Ovary (CHO) cells, COS cells, baculovirus) as is well known in the art, followed by protein purification. BMP9 and BMP10 are also commercially available from R&D Systems (Minneapolis, Minn.).

Accordingly, the disclosure provides methods of producing the subject BMP9 or BMP10 polypeptides. For example, a host cell transfected with an expression vector encoding a BMP9 or BMP10 polypeptide can be cultured under appropriate conditions to allow expression of the polypeptide to occur. The BMP9 or BMP10 polypeptide may be secreted and isolated from a mixture of cells and medium containing the BMP9 or BMP10 polypeptide. Alternatively, the polypeptide may be retained cytoplasmically or in a membrane fraction and the cells harvested, lysed and the protein isolated. A cell culture includes host cells, media and other byproducts. Suitable media for cell culture are well known in the art. The subject BMP9 or BMP10 polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the BMP9 or BMP10 polypeptides.

The disclosure further provides novel methods for purification of BMP9 or BMP10 polypeptides by using the affinity of these proteins for one or more of their receptors, including ALK1, ALK2, BMPR2, ActRIIA or ActRIIB A solid matrix (e.g., chromatography resin) may be joined to a ligand-binding portion of any of the foregoing to create an affinity matrix that will bind selectively to BMP9 or BMP10 polypeptides. The extracellular domain of the receptor may be fused to an Fc portion of an immunoglobulin and joined to a matrix containing an Fc binding protein, such as protein A. Surprisingly, a variant of an ActRIIB extracellular domain which contains an aspartic acid or glutamic acid rather than a leucine at position 79 is a particularly effective reagent for affinity purification of BMP9 or BMP10 polypeptides. Notably, this variant has reduced affinity for BMP9 or BMP10 relative to wild-type ActRIIB See the following published PCT patent applications for examples of receptors and receptor-Fc fusion constructs that are useful in the production of BMP9 or BMP10 polypeptides: WO 2011/020045, WO 2010/151426, WO 2010/019261, WO 2009/139891, WO 2009/134428, WO 2008/097541, WO 2008/076437, WO 2007/062188 and WO 2006/012627, the receptor and receptor-Fc sequences of which are incorporated by reference. ActRIIA, BMPR2 and ActRIIB reagents are useful for purifying BMP9 or BMP10 mature proteins, as these proteins will compete with the propeptide for binding to the mature portion. ALK1 or ALK2 reagents are useful for purifying BMP9 or BMP10 polypeptides as complexes with the prodomain, as these bind at a site that is distinct and non-competitive relative to the propeptide.

In another embodiment, a fusion gene coding for a purification leader sequence, such as a poly-(His)/enterokinase cleavage site sequence at the N-terminus of the desired portion of the recombinant BMP9 or BMP10 polypeptide, can allow purification of the expressed fusion protein by affinity chromatography using a Ni' metal resin. The purification leader sequence can then be subsequently removed by treatment with enterokinase to provide the purified BMP9 or BMP10 polypeptide (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

3. Exemplary Therapeutic Uses

In certain embodiments, the BMP9 or BMP10 polypeptides of the present disclosure can be used to increase red blood cell levels in mammals such as rodents and primates, and particularly human patients. Additionally, BMP9 or BMP10 polypeptides may be used in combination with EPO receptor activators to achieve an increase in red blood cells at lower dose ranges or to achieve an overall higher level of RBCs or a greater response rate. This may be beneficial in reducing the known off-target effects and risks associated with high doses of EPO receptor activators. In certain embodiments, the present invention provides methods of treating or preventing anemia in an individual in need thereof by administering to the individual a therapeutically effective amount of a BMP9 or BMP10 polypeptide or a combination (or concomitant therapy) of a BMP9 or BMP10 polypeptide and a EPO receptor activator. These methods may be used for therapeutic and prophylactic treatments of mammals, and particularly humans.

The BMP9 or BMP10 polypeptides may be used in combination with EPO receptor activators to reduce the required dose of these activators in patients that are susceptible to adverse effects of EPO. The primary adverse effects of EPO are an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which related to hypertension, are headaches, influenza-like syndrome, obstruction of shunts, myocardial infarctions and cerebral convulsions due to thrombosis, hypertensive encephalopathy, and red cell blood cell applasia (Singibarti, (1994) J. Clin Investig 72(suppl 6), S36-S43; Horl et al. (2000) Nephrol Dial Transplant 15(suppl 4), 51-56; Delanty et al. (1997) Neurology 49, 686-689; Bunn (2002) N Engl J Med 346(7), 522-523).

The rapid effect on red blood cell levels of the BMP9 or BMP10 polypeptides disclosed herein indicate that these agents act by a different mechanism than EPO. Accordingly, these antagonists may be useful for increasing red blood cell and hemoglobin levels in patients that do not respond well to EPO. For example, a BMP9 or BMP10 polypeptide may be beneficial for a patient in which administration of a normal to increased (>300 IU/kg/week) dose of EPO does not result in the increase of hemoglobin level up to the target level. Patients with an inadequate EPO response are found for all types of anemia, but higher numbers of non-responders have been observed particularly frequently in patients with cancers and patients with end-stage renal disease. An inadequate response to EPO can be either constitutive (i.e. observed upon the first treatment with EPO) or acquired (e.g. observed upon repeated treatment with EPO).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established. In either case, prevention or treatment may be discerned in the diagnosis provided by a physician or other health care provider and the intended result of administration of the therapeutic agent.

As shown herein, BMP9 or BMP10 polypeptides, optionally combined with an EPO receptor activator, may be used to increase red blood cell, hemoglobin or reticulocyte levels in healthy individuals, and such BMP9 or BMP10 polypeptides may be used in selected patient populations. Examples of appropriate patient populations include those with undesirably low red blood cell or hemoglobin levels, such as patients having an anemia, and those that are at risk for developing undesirably low red blood cell or hemoglobin levels, such as those patients that are about to undergo major surgery or other procedures that may result in substantial blood loss. In one embodiment, a patient with adequate red blood cell levels is treated with a BMP9 or BMP10 polypeptide to increase red blood cell levels, and then blood is drawn and stored for later use in transfusions.

BMP9 or BMP10 polypeptides, optionally combined with an EPO receptor activator, disclosed herein may be used to increase red blood cell levels in patients having an anemia. When observing hemoglobin levels in humans, a level of less than normal for the appropriate age and gender category may be indicative of anemia, although individual variations are taken into account. For example, a hemoglobin level of 12 g/dl is generally considered the lower limit of normal in the general adult population. Potential causes include blood-loss, nutritional deficits, medication reaction, various problems with the bone marrow and many diseases. More particularly, anemia has been associated with a variety of disorders that include, for example, chronic renal failure, myelodysplastic syndrome, rheumatoid arthritis, bone marrow transplantation. Anemia may also be associated with the following conditions: solid tumors (e.g. breast cancer, lung cancer, colon cancer); tumors of the lymphatic system (e.g. chronic lymphocyte leukemia, non-Hodgkins and Hodgkins lymphomas); tumors of the hematopoietic system (e.g. leukemia, myelodysplastic syndrome, multiple myeloma); radiation therapy; chemotherapy (e.g. platinum containing regimens); inflammatory and autoimmune diseases, including, but not limited to, rheumatoid arthritis, other inflammatory arthritides, systemic lupus erythematosis (SLE), acute or chronic skin diseases (e.g. psoriasis), inflammatory bowel disease (e.g. Crohn's disease and ulcerative colitis); acute or chronic renal disease or failure including idiopathic or congenital conditions; acute or chronic liver disease; acute or chronic bleeding; situations where transfusion of red blood cells is not possible due to patient allo- or auto-antibodies and/or for religious reasons (e.g. some Jehovah's Witnesses); infections (e.g. malaria, osteomyelitis); hemoglobinopathies, including, for example, sickle cell disease, thalassemias; drug use or abuse, e.g. alcohol misuse; pediatric patients with anemia from any cause to avoid transfusion; and elderly patients or patients with underlying cardiopulmonary disease with anemia who cannot receive transfusions due to concerns about circulatory overload.

BMP9 or BMP10 polypeptides, optionally combined with an EPO receptor activator, would be appropriate for treating anemias of hypoproliferative bone marrrow, which are typically associated with little change in red blood cell (RBC) morphology. Hypoproliferative anemias include: 1) anemia of chronic disease, 2) anemia of kidney disease, and 3) anemia associated with hypometabolic states. In each of these types, endogenous erythropoietin levels are inappropriately low for the degree of anemia observed. Other hypoproliferative anemias include: 4) early-stage iron-deficient anemia, and 5) anemia caused by damage to the bone marrow. In these types, endogenous erythropoietin levels are appropriately elevated for the degree of anemia observed.

The most common type of anemia is anemia of chronic disease, which encompasses inflammation, infection, tissue injury, and conditions such as cancer, and is distinguished by both low erythropoietin levels and an inadequate response to erythropoietin in the bone marrow (Adamson, 2008, Harrison's Principles of Internal Medicine, 17th ed.; McGraw Hill, New York, pp 628-634). Many factors can contribute to cancer-related anemia. Some are associated with the disease process itself and the generation of inflamatory cytokines such as interleukin-1, interferon-gamma, and tumor necrosis factor (Bron et al., 2001, Semin Oncol 28(Suppl 8):1-6). Among its effects, inflammation induces the key iron-regulatory peptide hepcidin, thereby inhibiting iron export from macrophages and generally limiting iron availability for erythropoiesis (Ganz, 2007, J Am Soc Nephrol 18:394-400). Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality.

Chronic kidney disease is associated with hypoproliferative anemia that varies in severity with the degree of renal impairment. Such anemia is primarily due to inadequate production of erythropoietin and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function (Levin et al., 1999, Am J Kidney Dis 27:347-354; Nissenson, 1992, Am J Kidney Dis 20(Suppl 1):21-24; Revicki et al., 1995, Am J Kidney Dis 25:548-554; Gafter et al., 1994, Kidney Int 45:224-231). A BMP9 or BMP10 polypeptide, optionally combined with an EPO receptor activator, can be used to treat anemia of kidney disease.

Many conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. Mild-to-moderate anemia can also occur with reduced dietary intake of protein, a condition particularly prevalent in the elderly. Finally, anemia can develop in patients with chronic liver disease arising from nearly any cause (Adamson, 2008, Harrison's Principles of Internal Medicine, 17th ed.; McGraw Hill, New York, pp 628-634).

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. A BMP9 or BMP10 polypeptide, optionally combined with an EPO receptor activator, can be used to speed recovery from anemia of acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs (Adamson, 2008, Harrison's Principles of Internal Medicine, 17th ed.; McGraw Hill, New York, pp 628-634). Appropriate therapy for iron-deficiency anemia depends on its cause and severity, with oral iron preparations, parenteral iron formulations, and RBC transfusion as major conventional options. A BMP9 or BMP10 polypeptide, optionally combined with an EPO receptor activator, could be used to treat chronic iron-deficiency anemias alone or in combination with conventional therapeutic approaches, particularly to treat anemias of multifactorial origin.

Hypoproliferative anemias can result from primary dysfunction or failure of the bone marrow, instead of dysfunction secondary to inflammation, infection, or cancer progression. Prominent examples would be myelosuppression caused by cancer chemotherapeutic drugs or cancer radiation therapy. A broad review of clinical trials found that mild anemia can occur in 100% of patients after chemotherapy, while more severe anemia can occur in up to 80% of such patients (Groopman et al., 1999, J Natl Cancer Inst 91:1616-1634). Myelosuppressive drugs include: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). A BMP9 or BMP10 polypeptide, optionally combined with an EPO receptor activator, can be used to treat anemia caused by chemotherapeutic agents and/or radiation therapy.

BMP9 or BMP10 polypeptides, optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

Patients may be treated with a dosing regimen intended to restore the patient to a target hemoglobin level, usually between about 10 g/dl and about 12.5 g/dl, and typically about 11.0 g/dl (see also Jacobs et al. (2000) Nephrol Dial Transplant 15, 15-19), although lower target levels may cause fewer cardiovascular side effects. Alternatively, hematocrit levels (percentage of the volume of a blood sample occupied by the cells) can be used as a measure for the condition of red blood cells. Hematocrit levels for healthy individuals range from 41 to 51% for adult males and from 35 to 45% for adult females. Target hematocrit levels are usually around 30-33%. Moreover, hemoglobin/hematocrit levels vary from person to person. Thus, optimally, the target hemoglobin/hematocrit level can be individualized for each patient.

In certain embodiments, the present invention provides methods for managing a patient that has been treated with, or is a candidate to be treated with, a BMP9 or BMP10 polypeptide by measuring one or more hematologic parameters in the patient. The hematologic parameters may be used to evaluate appropriate dosing for a patient who is a candidate to be treated with a BMP9 or BMP10 polypeptide, to monitor the hematologic parameters during treatment with a BMP9 or BMP10 polypeptide, to evaluate whether to adjust the dosage during treatment with a BMP9 or BMP10 polypeptide, and/or to evaluate an appropriate maintenance dose of a BMP9 or BMP10 polypeptide. If one or more of the hematologic parameters are outside the normal level, dosing with a BMP9 or BMP10 polypeptide may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range, or on the high side of normal, in a patient who is a candidate to be treated with a BMP9 or BMP10 polypeptide then onset of administration of the polypeptide may be delayed until the hematologic parameters have returned to a normal or acceptable level either naturally or via therapeutic intervention. For example, if a candidate patient is hypertensive or prehypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the BMP9 or BMP10 polypeptide may be delayed until the levels have returned to a normal or acceptable level.

In certain embodiments, if one or more hematologic parameters are outside the normal range, or on the high side of normal, in a patient who is a candidate to be treated with a BMP9 or BMP10 polypeptide then the onset of administration may be delayed. However, the dosage amount or frequency of dosing of the BMP9 or BMP10 polypeptide may be set at an amount that would reduce the risk of an unacceptable increase in the hematologic parameters arising upon administration of the BMP9 or BMP10 polypeptide. Alternatively, a therapeutic regimen may be developed for the patient that combines a BMP9 or BMP10 polypeptide with a therapeutic agent that addresses the undesirable level of the hematologic parameter. For example, if the patient has elevated blood pressure, or the BMP9 or BMP10 polypeptide appears to be causing elevated blood pressure, then a therapeutic regimen involving administration of a BMP9 or BMP10 polypeptide and a blood pressure lowering agent may be designed. For a patient having lower than desired iron stores, a therapeutic regimen of a BMP9 or BMP10 polypeptide and iron supplementation may be developed.

In one embodiment, baseline parameter(s) for one or more hematologic parameters may be established for a patient who is a candidate to be treated with a BMP9 or BMP10 polypeptide and an appropriate dosing regimen establish for that patient based on the baseline value(s). Alternatively, established baseline parameters based on a patient's medical history could be used to inform an appropriate BMP9 or BMP10 polypeptide dosing regimen for a patient. For example, if a healthy patient has an established baseline blood pressure reading that is above the defined normal range it may not be necessary to bring the patient's blood pressure into the range that is considered normal for the general population prior to treatment with the BMP9 or BMP10 polypeptide. A patient's baseline values for one or more hematologic parameters prior to treatment with a BMP9 or BMP10 polypeptide may also be used as the relevant comparative values for monitoring any changes to the hematologic parameters during treatment with the BMP9 or BMP10 polypeptide.

In certain embodiments, one or more hematologic parameters are measured in patients who are being treated with a BMP9 or BMP10 polypeptide. The hematologic parameters may be used to monitor the patient during treatment and permit adjustment or termination of the dosing with the BMP9 or BMP10 polypeptide or additional dosing with another therapeutic agent. For example, if administration of a BMP9 or BMP10 polypeptide results in an increase in blood pressure, red blood cell level, or hemoglobin level, or a reduction in iron stores, then the dose of the BMP9 or BMP10 polypeptide may be reduced in amount or frequency in order to decrease the effects of the BMP9 or BMP10 polypeptide on the one or more hematologic parameters. If administration or a BMP9 or BMP10 polypeptide results in a change in one or more hematologic parameters that is adverse to the patient, then the dosing of the BMP9 or BMP10 polypeptide may be terminated either temporarily, until the hematologic parameter(s) return to an acceptable level, or permanently. Similarly, if one or more hematologic parameters are not brought within an acceptable range after reducing the dose or frequency of administration of the BMP9 or BMP10 polypeptide then the dosing may be terminated. As an alternative, or in addition to, reducing or terminating the dosing with the BMP9 or BMP10 polypeptide, the patient may be dosed with an additional therapeutic agent that addresses the undesirable level in the hematologic parameter(s), such as, for example, a blood pressure lowering agent or an iron supplement. For example, if a patient being treated with a BMP9 or BMP10 polypeptide has elevated blood pressure, then dosing with the BMP9 or BMP10 polypeptide may continue at the same level and a blood pressure lowering agent is added to the treatment regimen, dosing with the BMP9 or BMP10 polypeptide may be reduce (e.g., in amount and/or frequency) and a blood pressure lowering agent is added to the treatment regimen, or dosing with the BMP9 or BMP10 polypeptide may be terminated and the patient may be treated with a blood pressure lowering agent.

4. Pharmaceutical Preparations

In certain embodiments, BMP9 or BMP10 polypeptides of the present invention are formulated with a pharmaceutically acceptable carrier. For example, a BMP9 or BMP10 polypeptide can be administered alone or as a component of a pharmaceutical preparation. The subject compounds may be formulated for administration in any convenient way for use in human or veterinary medicine. As noted above, it may be desirable to prepare a BMP9 or BMP10 polypeptide in a formulation comprising a prodomain polypeptide.

In certain embodiments, the therapeutic method of the invention includes administering the preparation systemically, or locally as an implant or device. When administered, the pharmaceutical preparation for use in this invention is, of course, in a pyrogen-free, physiologically acceptable form. Therapeutically useful agents other than the BMP9 or BMP10 polypeptides which may also optionally be included in the preparation as described above, may be administered simultaneously or sequentially with the subject BMP9 or BMP10 polypeptides.

Typically, compounds will be administered parenterally. Pharmaceutical preparations suitable for parenteral administration may comprise one or more BMP9 or BMP10 polypeptides in combination with one or more pharmaceutically acceptable sterile isotonic aqueous or nonaqueous solutions, dispersions, suspensions or emulsions, or sterile powders (e.g., lyophilates) which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, sugars, ethanol, polyols (such as glycerol, propylene glycol, polyethylene glycol, and the like), and suitable mixtures thereof, vegetable oils, such as olive oil, and injectable organic esters, such as ethyl oleate.

Further, the preparation may be encapsulated or injected in a form for delivery to a target tissue site. In certain embodiments, preparations of the present invention may include a matrix capable of delivering one or more therapeutic compounds (e.g., BMP9 or BMP10 polypeptides) to a target tissue site, providing a structure for the developing tissue and optimally capable of being resorbed into the body. For example, the matrix may provide slow release of the BMP9 or BMP10 polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

It is understood that the dosage regimen will be determined by the attending physician considering various factors which modify the action of the BMP9 or BMP10 polypeptides. The various factors include, but are not limited to, the patient's red blood cell count, hemoglobin level, systolic or diastolic blood pressure or other diagnostic assessments, the desired target red blood cell count, the patient's age, sex, and diet, the severity of any disease that may be contributing to a depressed red blood cell level, time of administration, and other clinical factors. The addition of other known growth factors to the final composition may also affect the dosage. Progress can be monitored by periodic assessment of red blood cell and hemoglobin levels, as well as assessments of reticulocyte levels and other indicators of the hematopoietic process.

In certain embodiments, the present invention also provides gene therapy for the in vivo production of BMP9 or BMP10 polypeptides. Such therapy would achieve its therapeutic effect by introduction of the BMP9 or BMP10 polynucleotide sequences into cells or tissues having the disorders as listed above. Delivery of BMP9 or BMP10 polynucleotide sequences can be achieved using a recombinant expression vector such as a chimeric virus or a colloidal dispersion system. Preferred for therapeutic delivery of BMP9 or BMP10 polynucleotide sequences is the use of targeted liposomes.

Various viral vectors which can be utilized for gene therapy as taught herein include adenovirus, herpes virus, vaccinia, or an RNA virus such as a retrovirus. The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the BMP9 or BMP10 polynucleotide.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of a BMP9 or BMP10 Polypeptide

BMP9 or BMP10 may be purchased from a commercial supplier, such as R&D Systems (Minneapolis, Minn.). Alternatively, a protocol such as the following may be followed:

A human BMP-9 (bBMP9) cDNA construct was generated by replacing the native signal sequence of BMP-9 with the signal sequence of tissue plasminogen activator (tPA) or another signal sequence. Examples of leader sequences:
  (i) Honey bee melittin (HBML): MKFLVNVALVFMV-VYISYIYA (SEQ ID NO: 14)
  (ii) Tissue Plasminogen Activator (TPA): MDAMKR-GLCCVLLLCGAVFVSP (SEQ ID NO: 15)

The DNA sequence encoding the tPA signal sequence was fused in-frame with the DNA sequence encoding the pro-peptide/mature region of BMP-9. This cDNA sequence was cloned into the pAID4 vector to encode a protein with the following unprocessed sequence:

(SEQ ID NO: 16)

```
  1  MDAMKRGLCC VLLLCGAVFV SPGAKPLQSW GRGSAGGNAH SPLGVPGGGL

51  PEHTFNLKMF LENVKVDFLR SLNLSGVPSQ DKTRVEPPQY MIDLYNRYTS

101  DKSTTPASNI VRSFSMEDAI SITATEDFPR QKHILLFNIS IPRHEQITRA

151  ELRLYVSCQN HVDPSHDLKG SVVIYDVLDG TDAWDSATET KTFLVSQDIQ

201  DEGWETLEVS SAVKRWVRSD STKSKNKLEV TVESHRKGCD TLDISVPPGS

251  RNLPFFVVES NDHSSGTKET RLELREMISH EQESVLKKLS KDGSTEAGES

301  SHEEDTDGHV AAGSTLARRK RSAGAGSHCQ KTSLRVNFED IGWDSWIIAP

351  KEYEAYECKG GCFFPLADDV TPTKHAIVQT LVHLKFPTKV GKACCVPTKL

401  SPISVLYKDD MGVPTLKYHY EGMSVAECGC R
```

A BMP10 polypeptide expression cassette may be similarly produced:

```
                                                       (SEQ. ID. NO: 17)
  1    MDAMKRGLCC VLLLCGAVFV SPGASPIMNL EQSPLEEDMS LFGDVFSEQD GVDFNTLLQS

61    MKDEFLKTLN LSDIPTQDSA KVDPPEYMLE LYNKFATDRT SMPSANIIRS FKNEDLFSQP

121    VSFNGLRKYP LLFNVSIPHH EEVIMAELRL YTLVQRDRMI YDGVDRKITI FEVLESKGDN

181    EGERNMLVLV SGEIYGTNSE WETFDVTDAI RRWQKSGSST HQLEVHIESK HDEAEDASSG

241    RLEIDTSAQN KHNPLLIVFS DDQSSDKERK EELNEMISHE QLPELDNLGL DSFSSGPGEE

301    ALLQMRSNII YDSTARIRRN AKGNYCKRTP LYIDFKEIGW DSWIIAPPGY EAYECRGVCN

361    YPLAEHLTPT KHAIIQALVH LKNSQKASKA CCVPTKLEPI SILYLDKGVV TYKFKYEGMA

421    VSECGCR
```

BMP-9 constructs were be transfected into a CHO DUKX B11 cell line that has been engineered to express a soluble (secreted) form of PACE (Furin)(Genbank No. P09958). Co-expression of PACE facilitates propeptide cleavage of BMPs. Clones were selected in 10 nM methotrexate (MTX) followed by amplification in 50 nM MTX to increase expression. A high expressing clone was identified by dilution cloning and adapted to serum-free suspension growth to generate conditioned media for purification. Optionally, a ubiquitous chromatin opening element (UCOE) may be included in the vector to facilitate expression. See, e.g., Cytotechnology. 2002 January; 38(1-3):43-6.

Affinity purification was achieved by passage over an affinity column prepared by loading and cross-linking a protein A column (MAb SelectSure, GE Healthcare Life Sciences) with an altered ActRIIb-Fc fusion protein having the following sequence:

```
                                                      (SEQ ID NO: 18)
  1    ETRECIYYNA NWELERTNQS GLERCEGEQD KRLHCYASWR NSSGTIELVK

51    KGCWDDDFNC YDRQECVATE ENPQVYFCCC EGNFCNERFT HLPEAGGPEV

101    TYEPPPTGGG THTCPPCPAP ELLGGPSVFL FPPKPKDTLM ISRTPEVTCV

151    VVDVSHEDPE VKFNWYVDGV EVHNAKTKPR EEQYNSTYRV VSVLTVLHQD

201    WLNGKEYKCK VSNKALPAPI EKTISKAKGQ PREPQVYTLP PSREEMTKNQ

251    VSLTCLVKGF YPSDIAVEWE SNGQPENNYK TTPPVLDSDG SFFLYSKLTV

301    DKSRWQQGNV FSCSVMHEAL HNHYTQKSLS LSPGK
```

BMP-9 protein was eluted from the column with 0.1M glycine, pH 3.0. BMP10 may be prepared in the same manner. In the event that BMP9 or BMP10 is purified as a mixed solution of covalent and non-covalent dimers, the covalent and non-covalent forms may be separated using a reverse phase HPLC, such as a Vydac C4 column eluted with a gradient of 0 to 100% acetonitrile in the presence of 0.1% trifluoroacetic acid. Covalent/non-covalent dimer content may be assessed by comparison of reducing and non-reducing SDS-PAGE.

Example 2. Administration of BMP9 to Wild-type Mice

To explore the effects of BMP9 on erythropoiesis, 10 C57BL/6 mice were randomized (2 groups, 5 animals per group) to receive two doses of vehicle control (TBS containing 0.8 mM HCl and 0.1% BSA), or BMP9 (10 mg/kg) once daily for two days by intraperitoneal injection. Blood samples were taken via tail vein on the study termination date. At 48 hours post treatment whole blood was obtained to determine complete blood counts (CBCs).

BMP9 increased RBC number, Hemoglobin (HGB) level and Hematocrit (HCT) by 32%, 34% and 31%, respectively, compared to vehicle control suggesting that BMP9 treatments results in increased red blood cells. There were no substantial effects on white blood cells or other blood parameters.

This study demonstrated that BMP9 has a profound, selective and rapid effect in increasing levels of red blood cells in the bloodstream, as measured by erythrocyte count, hemoglobin level and hematocrit.

INCORPORATION BY REFERENCE

All publications and patents mentioned herein are hereby incorporated by reference in their entirety as if each indi-

We claim:

1. A method for increasing red blood cell levels in a patient, the method comprising administering to a patient in need thereof a polypeptide selected from the group consisting of a BMP9 polypeptide comprising an amino acid sequence that is at least 90% identical to the sequence of SEQ ID NO: 3 and a BMP10 polypeptide comprising an amino acid sequence that is at least 90% identical to the sequence of SEQ ID NO: 6, wherein the polypeptide binds to ALK1 and increases red blood cell levels when administered to the patient.

2. The method of claim 1, wherein the polypeptide is a BMP9 polypeptide that comprises an amino acid sequence that is at least 95% identical to the sequence of SEQ ID NO: 3.

3. The method of claim 2, wherein the BMP9 polypeptide comprises an amino acid sequence that is at least 97% identical to the sequence of SEQ ID NO.: 3.

4. The method of claim 2, wherein the BMP9 polypeptide comprises an amino acid sequence that is at least 98% identical to the sequence of SEQ ID NO: 3.

5. The method of claim 2, wherein the BMP9 polypeptide comprises an amino acid sequence that is at least 99% identical to the sequence of SEQ ID NO.: 3.

6. The method of claim 1, wherein the polypeptide is a BMP10 polypeptide that comprises an amino acid sequence that is at least 95% identical to the sequence of SEQ ID NO: 6.

7. The method of claim 6, wherein the BMP10 polypeptide comprises an amino acid sequence that is at least 97% identical to the sequence of SEQ ID NO.: 6.

8. The method of claim 6, wherein the BMP10 polypeptide comprises an amino acid sequence that is at least 98% identical to the sequence of SEQ ID NO: 6.

9. The method of claim 6, wherein the BMP10 polypeptide comprises an amino acid sequence that is at least 99% identical to the sequence of SEQ ID NO.: 6.

10. The method of claim 1, wherein the BMP9 polypeptide or BMP10 polypeptide is administered in a pharmaceutical preparation.

11. The method of claim 10, wherein the pharmaceutical preparation comprises a prodomain polypeptide selected from the group consisting of a BMP9 prodomain polypeptide and a BMP10 prodomain polypeptide.

12. The method of claim 11, wherein the prodomain polypeptide is a BMP9 prodomain polypeptide.

13. The method of claim 12, wherein the prodomain polypeptide comprises an amino acid sequence that is at least 80% identical to the sequence of amino acids 23-319 of SEQ ID NO.: 1.

14. The method of claim 12, wherein the prodomain polypeptide comprises the amino acid sequence of amino acids 23-319 of SEQ ID NO.: 1.

15. The method of claim 12, wherein the pharmaceutical preparation comprises a BMP9 polypeptide noncovalently associated with the BMP9 prodomain polypeptide.

16. The method of claim 12, wherein the pharmaceutical preparation comprises a BMP10 polypeptide noncovalently associated with the BMP9 prodomain polypeptide.

17. The method of claim 11, wherein the prodomain polypeptide is a BMP10 prodomain polypeptide.

18. The method of claim 17, wherein the prodomain polypeptide comprises an amino acid sequence that is at least 80% identical to the sequence of amino acids 22-316 of SEQ ID NO.: 4.

19. The method of claim 17, wherein the prodomain polypeptide comprises the amino acid sequence of amino acids 22-316 of SEQ ID NO.: 4.

* * * * *

SEQUENCE LISTING

```
<160> NUMBER OF SEQ ID NOS: 18

<210> SEQ ID NO 1
<211> LENGTH: 429
<212> TYPE: PRT
<213> ORGANISM: Homo sapiens

<400> SEQUENCE: 1

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
        35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
            100                 105                 110

Ser Met Glu Asp Ala Ile Ser Ile Thr Ala Thr Glu Asp Phe Pro Phe
        115                 120                 125

Gln Lys His Ile Leu Leu Phe Asn Ile Ser Ile Pro Arg His Glu Gln
    130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
        195                 200                 205

Ser Ala Val Lys Arg Trp Val Arg Ser Asp Ser Thr Lys Ser Lys Asn
    210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
    290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335
```

```
Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
            355                 360                 365

Thr Pro Thr Lys His Ala Ile Val Gln Thr Leu Val His Leu Lys Phe
    370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
            420                 425

<210> SEQ ID NO 2
<211> LENGTH: 407
<212> TYPE: PRT
<213> ORGANISM: Homo sapiens

<400> SEQUENCE: 2

Lys Pro Leu Gln Ser Trp Gly Arg Gly Ser Ala Gly Gly Asn Ala His
1               5                   10                  15

Ser Pro Leu Gly Val Pro Gly Gly Leu Pro Glu His Thr Phe Asn
            20                  25                  30

Leu Lys Met Phe Leu Glu Asn Val Lys Val Asp Phe Leu Arg Ser Leu
            35                  40                  45

Asn Leu Ser Gly Val Pro Ser Gln Asp Lys Thr Arg Val Glu Pro Pro
50                  55                  60

Gln Tyr Met Ile Asp Leu Tyr Asn Arg Tyr Thr Ser Asp Lys Ser Thr
65                  70                  75                  80

Thr Pro Ala Ser Asn Ile Val Arg Ser Phe Ser Met Glu Asp Ala Ile
                85                  90                  95

Ser Ile Thr Ala Thr Glu Asp Phe Pro Phe Gln Lys His Ile Leu Leu
            100                 105                 110

Phe Asn Ile Ser Ile Pro Arg His Glu Gln Ile Thr Arg Ala Glu Leu
            115                 120                 125

Arg Leu Tyr Val Ser Cys Gln Asn His Val Asp Pro Ser His Asp Leu
    130                 135                 140

Lys Gly Ser Val Val Ile Tyr Asp Val Leu Asp Gly Thr Asp Ala Trp
145                 150                 155                 160

Asp Ser Ala Thr Glu Thr Lys Thr Phe Leu Val Ser Gln Asp Ile Gln
                165                 170                 175

Asp Glu Gly Trp Glu Thr Leu Glu Val Ser Ser Ala Val Lys Arg Trp
            180                 185                 190

Val Arg Ser Asp Ser Thr Lys Ser Lys Asn Lys Leu Glu Val Thr Val
            195                 200                 205

Glu Ser His Arg Lys Gly Cys Asp Thr Leu Asp Ile Ser Val Pro Pro
    210                 215                 220

Gly Ser Arg Asn Leu Pro Phe Phe Val Val Phe Ser Asn Asp His Ser
225                 230                 235                 240

Ser Gly Thr Lys Glu Thr Arg Leu Glu Leu Arg Glu Met Ile Ser His
                245                 250                 255

Glu Gln Glu Ser Val Leu Lys Lys Leu Ser Lys Asp Gly Ser Thr Glu
            260                 265                 270

Ala Gly Glu Ser Ser His Glu Glu Asp Thr Asp Gly His Val Ala Ala
```

```
                275                 280                 285
Gly Ser Thr Leu Ala Arg Arg Lys Arg Ser Ala Gly Ala Gly Ser His
    290                 295                 300

Cys Gln Lys Thr Ser Leu Arg Val Asn Phe Glu Asp Ile Gly Trp Asp
305                 310                 315                 320

Ser Trp Ile Ile Ala Pro Lys Glu Tyr Glu Ala Tyr Glu Cys Lys Gly
                325                 330                 335

Gly Cys Phe Phe Pro Leu Ala Asp Asp Val Thr Pro Thr Lys His Ala
            340                 345                 350

Ile Val Gln Thr Leu Val His Leu Lys Phe Pro Thr Lys Val Gly Lys
                355                 360                 365

Ala Cys Cys Val Pro Thr Lys Leu Ser Pro Ile Ser Val Leu Tyr Lys
        370                 375                 380

Asp Asp Met Gly Val Pro Thr Leu Lys Tyr His Tyr Glu Gly Met Ser
385                 390                 395                 400

Val Ala Glu Cys Gly Cys Arg
                405

<210> SEQ ID NO 3
<211> LENGTH: 110
<212> TYPE: PRT
<213> ORGANISM: Homo sapiens

<400> SEQUENCE: 3

Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
                20                  25                  30

Glu Ala Tyr Glu Cys Lys Gly Gly Cys Phe Phe Pro Leu Ala Asp Asp
            35                  40                  45

Val Thr Pro Thr Lys His Ala Ile Val Gln Thr Leu Val His Leu Lys
        50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110

<210> SEQ ID NO 4
<211> LENGTH: 424
<212> TYPE: PRT
<213> ORGANISM: Homo sapiens

<400> SEQUENCE: 4

Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
                20                  25                  30

Glu Glu Asp Met Ser Leu Phe Gly Asp Val Phe Ser Glu Gln Asp Gly
            35                  40                  45

Val Asp Phe Asn Thr Leu Leu Gln Ser Met Lys Asp Glu Phe Leu Lys
        50                  55                  60

Thr Leu Asn Leu Ser Asp Ile Pro Thr Gln Asp Ser Ala Lys Val Asp
65                  70                  75                  80

Pro Pro Glu Tyr Met Leu Glu Leu Tyr Asn Lys Phe Ala Thr Asp Arg
```

```
                        85                  90                  95
Thr Ser Met Pro Ser Ala Asn Ile Ile Arg Ser Phe Lys Asn Glu Asp
                100                 105                 110

Leu Phe Ser Gln Pro Val Ser Phe Asn Gly Leu Arg Lys Tyr Pro Leu
            115                 120                 125

Leu Phe Asn Val Ser Ile Pro His His Glu Glu Val Ile Met Ala Glu
        130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
        195                 200                 205

Arg Trp Gln Lys Ser Gly Ser Ser Thr His Gln Leu Glu Val His Ile
    210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
            260                 265                 270

Met Ile Ser His Glu Gln Leu Pro Glu Leu Asp Asn Leu Gly Leu Asp
        275                 280                 285

Ser Phe Ser Ser Gly Pro Gly Glu Glu Ala Leu Leu Gln Met Arg Ser
    290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
            340                 345                 350

Arg Gly Val Cys Asn Tyr Pro Leu Ala Glu His Leu Thr Pro Thr Lys
        355                 360                 365

His Ala Ile Ile Gln Ala Leu Val His Leu Lys Asn Ser Gln Lys Ala
    370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420

<210> SEQ ID NO 5
<211> LENGTH: 403
<212> TYPE: PRT
<213> ORGANISM: Homo sapiens

<400> SEQUENCE: 5

Ser Pro Ile Met Asn Leu Glu Gln Ser Pro Leu Glu Glu Asp Met Ser
1               5                   10                  15

Leu Phe Gly Asp Val Phe Ser Glu Gln Asp Gly Val Asp Phe Asn Thr
            20                  25                  30
```

Leu Leu Gln Ser Met Lys Asp Glu Phe Leu Lys Thr Leu Asn Leu Ser
             35                  40                  45

Asp Ile Pro Thr Gln Asp Ser Ala Lys Val Asp Pro Pro Glu Tyr Met
 50                  55                  60

Leu Glu Leu Tyr Asn Lys Phe Ala Thr Asp Arg Thr Ser Met Pro Ser
 65                  70                  75                  80

Ala Asn Ile Ile Arg Ser Phe Lys Asn Glu Asp Leu Phe Ser Gln Pro
                 85                  90                  95

Val Ser Phe Asn Gly Leu Arg Lys Tyr Pro Leu Leu Phe Asn Val Ser
            100                 105                 110

Ile Pro His His Glu Glu Val Ile Met Ala Glu Leu Arg Leu Tyr Thr
            115                 120                 125

Leu Val Gln Arg Asp Arg Met Ile Tyr Asp Gly Val Asp Arg Lys Ile
130                 135                 140

Thr Ile Phe Glu Val Leu Glu Ser Lys Gly Asp Asn Glu Gly Glu Arg
145                 150                 155                 160

Asn Met Leu Val Leu Val Ser Gly Glu Ile Tyr Gly Thr Asn Ser Glu
                165                 170                 175

Trp Glu Thr Phe Asp Val Thr Asp Ala Ile Arg Arg Trp Gln Lys Ser
            180                 185                 190

Gly Ser Ser Thr His Gln Leu Glu Val His Ile Glu Ser Lys His Asp
        195                 200                 205

Glu Ala Glu Asp Ala Ser Ser Gly Arg Leu Glu Ile Asp Thr Ser Ala
    210                 215                 220

Gln Asn Lys His Asn Pro Leu Leu Ile Val Phe Ser Asp Asp Gln Ser
225                 230                 235                 240

Ser Asp Lys Glu Arg Lys Glu Glu Leu Asn Glu Met Ile Ser His Glu
                245                 250                 255

Gln Leu Pro Glu Leu Asp Asn Leu Gly Leu Asp Ser Phe Ser Ser Gly
            260                 265                 270

Pro Gly Glu Glu Ala Leu Leu Gln Met Arg Ser Asn Ile Ile Tyr Asp
        275                 280                 285

Ser Thr Ala Arg Ile Arg Arg Asn Ala Lys Gly Asn Tyr Cys Lys Arg
    290                 295                 300

Thr Pro Leu Tyr Ile Asp Phe Lys Glu Ile Gly Trp Asp Ser Trp Ile
305                 310                 315                 320

Ile Ala Pro Pro Gly Tyr Glu Ala Tyr Glu Cys Arg Gly Val Cys Asn
                325                 330                 335

Tyr Pro Leu Ala Glu His Leu Thr Pro Thr Lys His Ala Ile Ile Gln
            340                 345                 350

Ala Leu Val His Leu Lys Asn Ser Gln Lys Ala Ser Lys Ala Cys Cys
        355                 360                 365

Val Pro Thr Lys Leu Glu Pro Ile Ser Ile Leu Tyr Leu Asp Lys Gly
    370                 375                 380

Val Val Thr Tyr Lys Phe Lys Tyr Glu Gly Met Ala Val Ser Glu Cys
385                 390                 395                 400

Gly Cys Arg

<210> SEQ ID NO 6
<211> LENGTH: 108
<212> TYPE: PRT
<213> ORGANISM: Homo sapiens

<400> SEQUENCE: 6

```
Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
            20                  25                  30

Ala Tyr Glu Cys Arg Gly Val Cys Asn Tyr Pro Leu Ala Glu His Leu
        35                  40                  45

Thr Pro Thr Lys His Ala Ile Ile Gln Ala Leu Val His Leu Lys Asn
    50                  55                  60

Ser Gln Lys Ala Ser Lys Ala Cys Cys Val Pro Thr Lys Leu Glu Pro
65                  70                  75                  80

Ile Ser Ile Leu Tyr Leu Asp Lys Gly Val Val Thr Tyr Lys Phe Lys
                85                  90                  95

Tyr Glu Gly Met Ala Val Ser Glu Cys Gly Cys Arg
            100                 105
```

<210> SEQ ID NO 7
<211> LENGTH: 428
<212> TYPE: PRT
<213> ORGANISM: Mus sp.

<400> SEQUENCE: 7

```
Met Ser Pro Gly Ala Phe Arg Val Ala Leu Leu Pro Leu Phe Leu Leu
1               5                   10                  15

Val Cys Val Thr Gln Gln Lys Pro Leu Gln Asn Trp Glu Gln Ala Ser
            20                  25                  30

Pro Gly Glu Asn Ala His Ser Ser Leu Gly Leu Ser Gly Ala Gly Glu
        35                  40                  45

Glu Gly Val Phe Asp Leu Gln Met Phe Leu Glu Asn Met Lys Val Asp
    50                  55                  60

Phe Leu Arg Ser Leu Asn Leu Ser Gly Ile Pro Ser Gln Asp Lys Thr
65                  70                  75                  80

Arg Ala Glu Pro Pro Gln Tyr Met Ile Asp Leu Tyr Asn Arg Tyr Thr
                85                  90                  95

Thr Asp Lys Ser Ser Thr Pro Ala Ser Asn Ile Val Arg Ser Phe Ser
            100                 105                 110

Val Glu Asp Ala Ile Ser Thr Ala Ala Thr Glu Asp Phe Pro Phe Gln
        115                 120                 125

Lys His Ile Leu Ile Phe Asn Ile Ser Ile Pro Arg His Glu Gln Ile
    130                 135                 140

Thr Arg Ala Glu Leu Arg Leu Tyr Val Ser Cys Gln Asn Asp Val Asp
145                 150                 155                 160

Ser Thr His Gly Leu Glu Gly Ser Met Val Val Tyr Asp Val Leu Glu
                165                 170                 175

Asp Ser Glu Thr Trp Asp Gln Ala Thr Gly Thr Lys Thr Phe Leu Val
            180                 185                 190

Ser Gln Asp Ile Arg Asp Glu Gly Trp Glu Thr Leu Glu Val Ser Ser
        195                 200                 205

Ala Val Lys Arg Trp Val Arg Ala Asp Ser Thr Thr Asn Lys Asn Lys
    210                 215                 220

Leu Glu Val Thr Val Gln Ser His Arg Glu Ser Cys Asp Thr Leu Asp
225                 230                 235                 240

Ile Ser Val Pro Pro Gly Ser Lys Asn Leu Pro Phe Phe Val Val Phe
                245                 250                 255

Ser Asn Asp Arg Ser Asn Gly Thr Lys Glu Thr Arg Leu Glu Leu Lys
            260                 265                 270
```

```
Glu Met Ile Gly His Glu Gln Glu Thr Met Leu Val Lys Thr Ala Lys
            275                 280                 285

Asn Ala Tyr Gln Val Ala Gly Glu Ser Gln Glu Glu Glu Gly Leu Asp
    290                 295                 300

Gly Tyr Thr Ala Val Gly Pro Leu Leu Ala Arg Arg Lys Arg Ser Thr
305                 310                 315                 320

Gly Ala Ser Ser His Cys Gln Lys Thr Ser Leu Arg Val Asn Phe Glu
                325                 330                 335

Asp Ile Gly Trp Asp Ser Trp Ile Ile Ala Pro Lys Glu Tyr Asp Ala
                340                 345                 350

Tyr Glu Cys Lys Gly Gly Cys Phe Phe Pro Leu Ala Asp Asp Val Thr
            355                 360                 365

Pro Thr Lys His Ala Ile Val Gln Thr Leu Val His Leu Lys Phe Pro
        370                 375                 380

Thr Lys Val Gly Lys Ala Cys Cys Val Pro Thr Lys Leu Ser Pro Ile
385                 390                 395                 400

Ser Ile Leu Tyr Lys Asp Asp Met Gly Val Pro Thr Leu Lys Tyr His
                405                 410                 415

Tyr Glu Gly Met Ser Val Ala Glu Cys Gly Cys Arg
            420                 425

<210> SEQ ID NO 8
<211> LENGTH: 427
<212> TYPE: PRT
<213> ORGANISM: Gallus sp.

<400> SEQUENCE: 8

Met His Tyr Phe Gly Val Leu Ala Ala Leu Ser Val Phe Asn Ile Ile
1               5                   10                  15

Ala Cys Leu Thr Arg Gly Lys Pro Leu Glu Asn Trp Lys Lys Leu Pro
            20                  25                  30

Val Met Glu Glu Ser Asp Ala Phe Phe His Asp Pro Gly Glu Val Glu
        35                  40                  45

His Asp Thr His Phe Asp Phe Lys Ser Phe Leu Glu Asn Met Lys Thr
    50                  55                  60

Asp Leu Leu Arg Ser Leu Asn Leu Ser Arg Val Pro Ser Gln Val Lys
65                  70                  75                  80

Thr Lys Glu Glu Pro Pro Gln Phe Met Ile Asp Leu Tyr Asn Arg Tyr
                85                  90                  95

Thr Ala Asp Lys Ser Ser Ile Pro Ala Ser Asn Ile Val Arg Ser Phe
            100                 105                 110

Ser Thr Glu Asp Val Val Ser Leu Ile Ser Pro Glu Glu His Ser Phe
        115                 120                 125

Gln Lys His Ile Leu Leu Phe Asn Ile Ser Ile Pro Arg Tyr Glu Glu
    130                 135                 140

Val Thr Arg Ala Glu Leu Arg Ile Phe Ile Ser Cys His Lys Glu Val
145                 150                 155                 160

Gly Ser Pro Ser Arg Leu Glu Gly Asn Met Val Ile Tyr Asp Val Leu
                165                 170                 175

Asp Gly Asp His Trp Glu Asn Lys Glu Ser Thr Lys Ser Leu Leu Val
            180                 185                 190

Ser His Ser Ile Gln Asp Cys Gly Trp Glu Met Phe Glu Val Ser Ser
        195                 200                 205

Ala Val Lys Arg Trp Val Lys Ala Asp Lys Met Lys Thr Lys Asn Lys
```

```
                    210                 215                 220
Leu Glu Val Val Ile Glu Ser Lys Asp Leu Ser Gly Phe Pro Cys Gly
225                 230                 235                 240

Lys Leu Asp Ile Thr Val Thr His Asp Thr Lys Asn Leu Pro Leu Leu
                245                 250                 255

Ile Val Phe Ser Asn Asp Arg Ser Asn Gly Thr Lys Glu Thr Lys Val
                260                 265                 270

Glu Leu Arg Glu Met Ile Val His Glu Gln Glu Ser Val Leu Asn Lys
            275                 280                 285

Leu Gly Lys Asn Asp Ser Ser Ser Glu Glu Gln Arg Glu Glu Lys
290                 295                 300

Ala Ile Ala Arg Pro Arg Gln His Ser Ser Arg Ser Lys Arg Ser Ile
305                 310                 315                 320

Gly Ala Asn His Cys Arg Arg Thr Ser Leu His Val Asn Phe Lys Glu
                325                 330                 335

Ile Gly Trp Asp Ser Trp Ile Ile Ala Pro Lys Asp Tyr Glu Ala Phe
            340                 345                 350

Glu Cys Lys Gly Gly Cys Phe Phe Pro Leu Thr Asp Asn Val Thr Pro
            355                 360                 365

Thr Lys His Ala Ile Val Gln Thr Leu Val His Leu Gln Asn Pro Lys
            370                 375                 380

Lys Ala Ser Lys Ala Cys Cys Val Pro Thr Lys Leu Asp Ala Ile Ser
385                 390                 395                 400

Ile Leu Tyr Lys Asp Asp Ala Gly Val Pro Thr Leu Ile Tyr Asn Tyr
                405                 410                 415

Glu Gly Met Lys Val Ala Glu Cys Gly Cys Arg
                420                 425

<210> SEQ ID NO 9
<211> LENGTH: 421
<212> TYPE: PRT
<213> ORGANISM: Mus sp.

<400> SEQUENCE: 9

Met Gly Ser Leu Val Leu Pro Leu Ser Ala Val Phe Cys Leu Val Ala
1               5                   10                  15

His Ser Ala Ser Gly Ser Pro Ile Met Gly Leu Glu Gln Ser Pro Leu
                20                  25                  30

Glu Glu Asp Met Pro Phe Phe Asp Asp Ile Phe Thr Glu Gln Asp Gly
            35                  40                  45

Ile Asp Phe Asn Thr Leu Leu Gln Ser Met Lys Asn Glu Phe Leu Lys
50                  55                  60

Thr Leu Asn Leu Ser Asp Ile Pro Val Gln Asp Thr Gly Arg Val Asp
65                  70                  75                  80

Pro Pro Glu Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Asp
            100                 105                 110

Leu Phe Ser Gln Pro Val Thr Phe Asn Gly Leu Arg Lys Tyr Pro Leu
        115                 120                 125

Leu Phe Asn Val Ser Ile Pro His His Glu Glu Val Val Met Ala Glu
    130                 135                 140

Leu Arg Leu Tyr Thr Leu Val Gln Arg Asp Arg Met Met Tyr Asp Gly
145                 150                 155                 160
```

```
Val Asp Arg Lys Ile Thr Ile Phe Glu Val Leu Glu Ser Ala Asp Gly
            165                 170                 175

Ser Glu Glu Arg Ser Met Leu Val Leu Val Ser Thr Glu Ile Tyr
        180                 185                 190

Gly Thr Asn Ser Glu Trp Glu Thr Phe Asp Val Thr Asp Ala Thr Arg
        195                 200                 205

Arg Trp Gln Lys Ser Gly Pro Ser Thr His Gln Leu Glu Ile His Ile
    210                 215                 220

Glu Ser Arg Gln Asn Gln Ala Glu Asp Thr Gly Arg Gly Gln Leu Glu
225                 230                 235                 240

Ile Asp Met Ser Ala Gln Asn Lys His Asp Pro Leu Leu Val Val Phe
                245                 250                 255

Ser Asp Asp Gln Ser Asn Asp Lys Glu Gln Lys Glu Glu Leu Asn Glu
                260                 265                 270

Leu Ile Thr His Glu Gln Asp Leu Asp Leu Asp Ser Asp Ala Phe Phe
                275                 280                 285

Ser Gly Pro Asp Glu Glu Ala Leu Leu Gln Met Arg Ser Asn Met Ile
        290                 295                 300

Asp Asp Ser Ser Ala Arg Ile Arg Arg Asn Ala Lys Gly Asn Tyr Cys
305                 310                 315                 320

Lys Lys Thr Pro Leu Tyr Ile Asp Phe Lys Glu Ile Gly Trp Asp Ser
                325                 330                 335

Trp Ile Ile Ala Pro Pro Gly Tyr Glu Ala Tyr Glu Cys Arg Gly Val
                340                 345                 350

Cys Asn Tyr Pro Leu Ala Glu His Leu Thr Pro Thr Lys His Ala Ile
            355                 360                 365

Ile Gln Ala Leu Val His Leu Lys Asn Ser Gln Lys Ala Ser Lys Ala
        370                 375                 380

Cys Cys Val Pro Thr Lys Leu Asp Pro Ile Ser Ile Leu Tyr Leu Asp
385                 390                 395                 400

Lys Gly Val Val Thr Tyr Lys Phe Lys Tyr Glu Gly Met Ala Val Ser
                405                 410                 415

Glu Cys Gly Cys Arg
            420

<210> SEQ ID NO 10
<211> LENGTH: 425
<212> TYPE: PRT
<213> ORGANISM: Gallus sp.

<400> SEQUENCE: 10

Met Asp Ser Ile Val Leu Gln Leu Trp Ala Gly Leu Cys Leu Leu Val
1               5                   10                  15

His Leu Ala Thr Cys Ser Pro Ile Leu Ser Leu Glu His Ser Ser Leu
                20                  25                  30

Glu Glu Gly Glu Pro Leu Phe Asp Phe Leu Ser Glu Gln Asp Gly
            35                  40                  45

Val Asp Phe Asn Thr Leu Leu Gln Asn Met Lys Asn Glu Phe Leu Lys
    50                  55                  60

Thr Leu Asn Leu Ser Asp Ile Pro Leu His Glu Ser Ala Lys Val Asp
65                  70                  75                  80

Pro Pro Glu Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Asp
                100                 105                 110
```

Leu Ala Ser His Pro Val Gly Val Ile Gly Val Arg Lys Tyr Pro Leu
            115                 120                 125

Leu Phe Asn Val Ser Ile Pro His His Glu Glu Ile Thr Met Ala Glu
        130                 135                 140

Leu Arg Leu Tyr Thr Leu Val Glu Arg Asp Gln Met Leu Tyr Glu Gly
145                 150                 155                 160

Leu Asp Arg Lys Val Thr Ile Phe Glu Val Leu Glu Asn Asp His Met
                165                 170                 175

Gly Val Gly Glu Glu Arg Lys Ile Val Ala Leu Ala Ser Arg Gln Ile
            180                 185                 190

Tyr Gly Thr Ser Ser Glu Trp Glu Ser Phe Glu Val Thr Glu Ala Ile
        195                 200                 205

Arg Arg Trp Arg Arg Ala Gly Leu Thr Thr His Arg Leu Glu Val His
210                 215                 220

Ile Glu Ser Arg Glu Gly Glu Gln Asn Gly Glu Gly Lys Leu Asp
225                 230                 235                 240

Ile Asp Ile Asn Ser Glu Ala Lys His Val Pro Leu Leu Ile Val Phe
                245                 250                 255

Ser Asp Asp Gln Ser Asn Asp Gln Lys Glu Lys Gln Glu Leu Asn
            260                 265                 270

Glu Met Ile Asp His Glu Gln Leu Leu Asp Leu Glu Asn Leu Glu Val
        275                 280                 285

Gly Asn Phe His Gly His Pro Gly Glu Glu Ala Leu Leu Gln Met Arg
290                 295                 300

Ser Asn Ile Ile Tyr Asp Ser Thr Ala Arg Ile Arg Arg Asn Ala Lys
305                 310                 315                 320

Gly Asn Tyr Cys Lys Lys Thr Pro Leu Tyr Ile Asp Phe Lys Glu Ile
                325                 330                 335

Gly Trp Asp Ser Trp Ile Ile Ala Pro Ala Gly Tyr Glu Ala Tyr Glu
            340                 345                 350

Cys His Gly Val Cys Ala Tyr Pro Leu Thr Glu His Val Thr Pro Thr
        355                 360                 365

Lys His Ala Ile Val Gln Thr Leu Val His Leu Lys Asn Pro Gln Lys
370                 375                 380

Ala Ser Lys Ala Cys Cys Val Pro Thr Lys Leu Asp Pro Ile Ser Ile
385                 390                 395                 400

Leu Tyr Met Asp Ala Gly Val Val Thr Tyr Lys Phe Lys Tyr Glu Gly
                405                 410                 415

Met Val Val Ser Glu Cys Gly Cys Arg
            420                 425

<210> SEQ ID NO 11
<211> LENGTH: 1453
<212> TYPE: DNA
<213> ORGANISM: Homo sapiens

<400> SEQUENCE: 11
cggtccagcc cggcagcggg tgagagtggg tgctggccag gacggttcct tcagagcaaa      60 cagcaggag atgccggccc gctccttccc agctcctccc cgtgcccgct aacacagcac     120
ggccgcctgc agtctcctct ctgggtgatt gcgcgggcct aagatgtgtc ctggggcact     180
gtgggtggcc ctgcccctgc tgtccctgct ggctggctcc ctacagggga agccactgca     240
gagctgggga cgagggtctg ctgggggaaa cgcccacagc ccactggggg tgcctggagg     300

```
tgggctgcct gagcacacct tcaacctgaa gatgtttctg gagaacgtga aggtggattt      360
cctgcgcagc cttaacctga gtggggtccc ttcgcaggac aaaaccaggg tggagccgcc      420
gcagtacatg attgacctgt acaacaggta cacgtccgat aagtcgacta cgccagcgtc      480
caacattgtg cggagcttca gcatggaaga tgccatctcc ataactgcca cagaggactt      540 cccccttccag aagcacatct tgctcttcaa catctccatt cctaggcatg agcagatcac      600
cagagctgag ctccgactct atgtctcctg tcaaaatcac gtgggacccct ctcatgacct      660 gaaaggaagc gtggtcattt atgatgttct ggatggaaca gatgcctggg atagtgctac      720
agagaccaag accttcctgg tgtcccagga cattccagga tgagggctggg agaccttgga      780 agtgtccagc gccgtgaagc gctgggtccg gtccgactcc accaagagca aaaataagct      840
ggaagtgact gtggagagcc acaggaaggg ctgcgacacg ctggacatca gtgtccccccc    900 aggttccaga aacctgccct tctttgttgt cttctccaat gaccacagca gtgggaccaa      960
ggagaccagg ctggagctga gggagatgat cagccatgaa caagagagcg tgctcaagaa     1020
gctgtccaag gacggctcca cagaggcagt gagagcagt cacgaggagg acacggatgg      1080
ccacgtggct gcggggtcga cttttagcca gcggaaaagg agcgccgggg ctggcagcca      1140
ctgtcaaaag acctccctgc gggtaaactt cgaggacatc ggctgggaca gctggatcat     1200
tgcacccaag gagtatgaag cctacgagtg taagggcggc tgcttcttcc ccttggctga     1260
cgatgtgacg ccgacgaaac acgctatcgt gcagaccctg gtgcatctca gttccccac      1320 aaaggtgggc aaggcctgct gtgtgcccac caaactgagc cccatctccg tcctctacaa     1380
ggatgacatg ggggtgccca ccctcaagta ccattacgag ggcatgagcg tggcagagtg     1440
tgggtgcagg tag                                                        1453

<210> SEQ ID NO 12
<211> LENGTH: 1584
<212> TYPE: DNA
<213> ORGANISM: Homo sapiens

<400> SEQUENCE: 12
ggggagagga agagtggtag ggggaggag agagagagga agagtttcca aacttgtctc        60
cagtgacagg agacatttac gttccacaag ataaaactgc cacttagagc ccagggaagc      120
taaaccttcc tggcttggcc taggagctcg agcggagtca tgggctctct ggtcctgaca      180
ctgtgcgctc tttttctgcct ggcagcttac ttggtttctg gcagccccat catgaaccta     240
gagcagtctc ctctggaaga agatatgtcc ctctttggtg atgttttctc agagcaagac     300
ggtgtcgact ttaacacact gctccagagc atgaaggatg agtttcttaa gacactaaac     360
ctctctgaca tccccacgca ggattcagcc aaggtggacc caccagagta catgttggaa     420
ctctacaaca aatttgcaac agatcggacc tccatgccct ctgccaacat cattaggagt     480
ttcaagaatg aagatctgtt tccccagccg gtcagtttta tgggctccg aaaatacccc     540 ctcctcttca atgtgtccat tcctcaccat gaagaggtca tcatggctga acttaggcta     600
tacacactgg tgcaaaggga tcgtatgata tacgatggag tagaccggaa aattaccatt      660
tttgaagtgc tggagagcaa aggggataat gagggagaaa gaaacatgct ggtcttggtg     720
tctggggaga tatatggaac caacagtgag tgggagactt tgatgtcac agatgccatc     780 agacgttggc aaaagtcagg ctcatccacc caccagctgg aggtccacat tgagagcaaa     840
cacgatgaag ctgaggatgc cagcagtgga cggctagaaa tagataccag tgcccagaat     900
aagcataacc ctttgctcat cgtgttttct gatgaccaaa gcagtgacaa ggagaggaag     960
```

-continued

```
gaggaactga atgaaatgat ttcccatgag caacttccag agctggacaa cttgggcctg    1020
gatagctttt ccagtggacc tggggaagag gctttgttgc agatgagatc aaacatcatc    1080
tatgactcca ctgcccgaat cagaaggaac gccaaaggaa actactgtaa gaggaccccg    1140
ctctacatcg acttcaagga gattgggtgg gactcctgga tcatcgctcc gcctggatac    1200
gaagcctatg aatgccgtgg tgtttgtaac tacccctgg cagagcatct cacacccaca     1260
aagcatgcaa ttatccaggc cttggtccac ctcaagaatt cccagaaagc ttccaaagcc    1320
tgctgtgtgc ccacaaagct agagcccatc tccatcctct atttagacaa aggcgtcgtc    1380
acctacaagt ttaaatacga aggcatggcc gtctccgaat gtggctgtag atagaagaag    1440
agtcctatgg cttatttaat aactgtaaat gtgtatattt ggtgttccta tttaatgaga    1500
ttatttaata agggtgtaca gtaatagagg cttgctgcct tcaggaaatg gacaggtcag    1560
tttgttgtag gaaatgcata tttt                                          1584
```

```
<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5

<210> SEQ ID NO 14
<211> LENGTH: 21
<212> TYPE: PRT
<213> ORGANISM: Unknown
<220> FEATURE:
<223> OTHER INFORMATION: Description of Unknown: Honey bee melittin
      peptide

<400> SEQUENCE: 14

Met Lys Phe Leu Val Asn Val Ala Leu Val Phe Met Val Val Tyr Ile
1               5                   10                  15

Ser Tyr Ile Tyr Ala
            20

<210> SEQ ID NO 15
<211> LENGTH: 22
<212> TYPE: PRT
<213> ORGANISM: Unknown
<220> FEATURE:
<223> OTHER INFORMATION: Description of Unknown: Tissue Plasminogen
      Activator peptide

<400> SEQUENCE: 15

Met Asp Ala Met Lys Arg Gly Leu Cys Cys Val Leu Leu Leu Cys Gly
1               5                   10                  15

Ala Val Phe Val Ser Pro
            20

<210> SEQ ID NO 16
<211> LENGTH: 431
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 16

```
Met Asp Ala Met Lys Arg Gly Leu Cys Cys Val Leu Leu Leu Cys Gly
1               5                   10                  15

Ala Val Phe Val Ser Pro Gly Ala Lys Pro Leu Gln Ser Trp Gly Arg
            20                  25                  30

Gly Ser Ala Gly Gly Asn Ala His Ser Pro Leu Gly Val Pro Gly Gly
        35                  40                  45

Gly Leu Pro Glu His Thr Phe Asn Leu Lys Met Phe Leu Glu Asn Val
    50                  55                  60

Lys Val Asp Phe Leu Arg Ser Leu Asn Leu Ser Gly Val Pro Ser Gln
65                  70                  75                  80

Asp Lys Thr Arg Val Glu Pro Pro Gln Tyr Met Ile Asp Leu Tyr Asn
                85                  90                  95

Arg Tyr Thr Ser Asp Lys Ser Thr Thr Pro Ala Ser Asn Ile Val Arg
            100                 105                 110

Ser Phe Ser Met Glu Asp Ala Ile Ser Ile Thr Ala Thr Glu Asp Phe
        115                 120                 125

Pro Phe Gln Lys His Ile Leu Leu Phe Asn Ile Ser Ile Pro Arg His
    130                 135                 140

Glu Gln Ile Thr Arg Ala Glu Leu Arg Leu Tyr Val Ser Cys Gln Asn
145                 150                 155                 160

His Val Asp Pro Ser His Asp Leu Lys Gly Ser Val Val Ile Tyr Asp
                165                 170                 175

Val Leu Asp Gly Thr Asp Ala Trp Asp Ser Ala Thr Glu Thr Lys Thr
            180                 185                 190

Phe Leu Val Ser Gln Asp Ile Gln Asp Glu Gly Trp Glu Thr Leu Glu
        195                 200                 205

Val Ser Ser Ala Val Lys Arg Trp Val Arg Ser Asp Ser Thr Lys Ser
    210                 215                 220

Lys Asn Lys Leu Glu Val Thr Val Glu Ser His Arg Lys Gly Cys Asp
225                 230                 235                 240

Thr Leu Asp Ile Ser Val Pro Pro Gly Ser Arg Asn Leu Pro Phe Phe
                245                 250                 255

Val Val Phe Ser Asn Asp His Ser Ser Gly Thr Lys Glu Thr Arg Leu
            260                 265                 270

Glu Leu Arg Glu Met Ile Ser His Glu Gln Glu Ser Val Leu Lys Lys
        275                 280                 285

Leu Ser Lys Asp Gly Ser Thr Glu Ala Gly Glu Ser Ser His Glu Glu
    290                 295                 300

Asp Thr Asp Gly His Val Ala Ala Gly Ser Thr Leu Ala Arg Arg Lys
305                 310                 315                 320

Arg Ser Ala Gly Ala Gly Ser His Cys Gln Lys Thr Ser Leu Arg Val
                325                 330                 335

Asn Phe Glu Asp Ile Gly Trp Asp Ser Trp Ile Ile Ala Pro Lys Glu
            340                 345                 350

Tyr Glu Ala Tyr Glu Cys Lys Gly Gly Cys Phe Phe Pro Leu Ala Asp
        355                 360                 365

Asp Val Thr Pro Thr Lys His Ala Ile Val Gln Thr Leu Val His Leu
    370                 375                 380

Lys Phe Pro Thr Lys Val Gly Lys Ala Cys Cys Val Pro Thr Lys Leu
385                 390                 395                 400

Ser Pro Ile Ser Val Leu Tyr Lys Asp Asp Met Gly Val Pro Thr Leu
```

```
                    405                 410                 415
Lys Tyr His Tyr Glu Gly Met Ser Val Ala Glu Cys Gly Cys Arg
                420                 425                 430

<210> SEQ ID NO 17
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Ala Met Lys Arg Gly Leu Cys Cys Val Leu Leu Leu Cys Gly
1               5                   10                  15

Ala Val Phe Val Ser Pro Gly Ala Ser Pro Ile Met Asn Leu Glu Gln
                20                  25                  30

Ser Pro Leu Glu Glu Asp Met Ser Leu Phe Gly Asp Val Phe Ser Glu
            35                  40                  45

Gln Asp Gly Val Asp Phe Asn Thr Leu Leu Gln Ser Met Lys Asp Glu
    50                  55                  60

Phe Leu Lys Thr Leu Asn Leu Ser Asp Ile Pro Thr Gln Asp Ser Ala
65                  70                  75                  80

Lys Val Asp Pro Pro Glu Tyr Met Leu Glu Leu Tyr Asn Lys Phe Ala
                85                  90                  95

Thr Asp Arg Thr Ser Met Pro Ser Ala Asn Ile Ile Arg Ser Phe Lys
            100                 105                 110

Asn Glu Asp Leu Phe Ser Gln Pro Val Ser Phe Asn Gly Leu Arg Lys
        115                 120                 125

Tyr Pro Leu Leu Phe Asn Val Ser Ile Pro His His Glu Glu Val Ile
    130                 135                 140

Met Ala Glu Leu Arg Leu Tyr Thr Leu Val Gln Arg Asp Arg Met Ile
145                 150                 155                 160

Tyr Asp Gly Val Asp Arg Lys Ile Thr Ile Phe Glu Val Leu Glu Ser
                165                 170                 175

Lys Gly Asp Asn Glu Gly Glu Arg Asn Met Leu Val Leu Val Ser Gly
            180                 185                 190

Glu Ile Tyr Gly Thr Asn Ser Glu Trp Glu Thr Phe Asp Val Thr Asp
        195                 200                 205

Ala Ile Arg Arg Trp Gln Lys Ser Gly Ser Ser Thr His Gln Leu Glu
    210                 215                 220

Val His Ile Glu Ser Lys His Asp Glu Ala Glu Asp Ala Ser Ser Gly
225                 230                 235                 240

Arg Leu Glu Ile Asp Thr Ser Ala Gln Asn Lys His Asn Pro Leu Leu
                245                 250                 255

Ile Val Phe Ser Asp Asp Gln Ser Ser Asp Lys Glu Arg Lys Glu Glu
            260                 265                 270

Leu Asn Glu Met Ile Ser His Glu Gln Leu Pro Glu Leu Asp Asn Leu
        275                 280                 285

Gly Leu Asp Ser Phe Ser Ser Gly Pro Gly Glu Glu Ala Leu Leu Gln
    290                 295                 300

Met Arg Ser Asn Ile Ile Tyr Asp Ser Thr Ala Arg Ile Arg Arg Asn
305                 310                 315                 320

Ala Lys Gly Asn Tyr Cys Lys Arg Thr Pro Leu Tyr Ile Asp Phe Lys
                325                 330                 335
```

```
Glu Ile Gly Trp Asp Ser Trp Ile Ile Ala Pro Pro Gly Tyr Glu Ala
                340                 345                 350

Tyr Glu Cys Arg Gly Val Cys Asn Tyr Pro Leu Ala Glu His Leu Thr
            355                 360                 365

Pro Thr Lys His Ala Ile Ile Gln Ala Leu Val His Leu Lys Asn Ser
        370                 375                 380

Gln Lys Ala Ser Lys Ala Cys Cys Val Pro Thr Lys Leu Glu Pro Ile
385                 390                 395                 400

Ser Ile Leu Tyr Leu Asp Lys Gly Val Val Thr Tyr Lys Phe Lys Tyr
                405                 410                 415

Glu Gly Met Ala Val Ser Glu Cys Gly Cys Arg
            420                 425

<210> SEQ ID NO 18
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
                100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270
```

```
Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335
```